(12) United States Patent
Chae et al.

(10) Patent No.: US 11,647,776 B2
(45) Date of Patent: May 16, 2023

(54) EXTRACT, CONSUMABLE PRODUCT AND METHOD FOR ENRICHING BIOACTIVE METABOLITE IN AN EXTRACT

(71) Applicant: Brightseed, Inc., South San Francisco, CA (US)

(72) Inventors: Lee Heil Chae, San Francisco, CA (US); James Flatt, San Francisco, CA (US); Alexandra Marcela Herrmann, San Francisco, CA (US); Gabriel Navarro, San Francisco, CA (US); Jessica Leigh Ochoa, San Francisco, CA (US)

(73) Assignee: Brightseed, Inc., South San Francisco, CA (US)

( * ) Notice: Subject to any disclaimer, the term of this patent is extended or adjusted under 35 U.S.C. 154(b) by 0 days.

(21) Appl. No.: 17/525,573

(22) Filed: Nov. 12, 2021

(65) Prior Publication Data
US 2022/0061370 A1 Mar. 3, 2022

Related U.S. Application Data

(63) Continuation of application No. PCT/US2020/059726, filed on Nov. 9, 2020.

(60) Provisional application No. 62/933,660, filed on Nov. 11, 2019.

(51) Int. Cl.
| A23L 33/105 | (2016.01) |
| A61K 31/165 | (2006.01) |
| A61K 31/13 | (2006.01) |
| A61K 36/81 | (2006.01) |
| A01H 3/00 | (2006.01) |
| A01H 3/02 | (2006.01) |
| A01H 3/04 | (2006.01) |

(52) U.S. Cl.
CPC .......... *A23L 33/105* (2016.08); *A61K 31/165* (2013.01); *A01H 3/00* (2013.01); *A01H 3/02* (2013.01); *A01H 3/04* (2013.01); *A23V 2300/14* (2013.01); *A61K 31/13* (2013.01); *A61K 36/81* (2013.01); *A61K 2236/11* (2013.01); *C12Y 203/0111* (2013.01)

(58) Field of Classification Search
CPC .............. A61K 2236/00; C12Y 203/01; A23V 2002/00; A23V 2300/00; A23L 33/105
See application file for complete search history.

(56) References Cited

U.S. PATENT DOCUMENTS

| 5,605,793 A | 2/1997 | Stemmer |
| 5,811,238 A | 9/1998 | Stemmer et al. |
| 5,830,721 A | 11/1998 | Stemmer et al. |
| 5,837,458 A | 11/1998 | Minshull et al. |
| 6,265,185 B1 | 7/2001 | Muller et al. |
| 6,316,209 B1 | 11/2001 | Baekkeskov et al. |
| 6,368,837 B1 | 4/2002 | Gatenby et al. |
| 6,391,651 B1 | 5/2002 | Maclaren et al. |
| 6,521,748 B2 | 2/2003 | Tang |
| 7,666,455 B2 | 2/2010 | Resurreccion et al. |
| 8,481,593 B2 | 7/2013 | Okombi |
| 9,089,499 B2 | 7/2015 | Okombi et al. |
| 9,227,898 B2 | 1/2016 | Boue et al. |
| 10,334,689 B2 | 6/2019 | Brebenel |
| 10,344,869 B2 | 7/2019 | Collins et al. |
| 11,173,136 B2 | 11/2021 | Chae |
| 11,382,880 B2 | 7/2022 | Chae et al. |
| 2003/0152682 A1 | 8/2003 | Ley |
| 2004/0198656 A1 | 10/2004 | Najib et al. |
| 2004/0234657 A1 | 11/2004 | Rowley et al. |
| 2007/0183996 A1 | 8/2007 | Okombi |
| 2008/0132544 A1 | 6/2008 | Kitano |
| 2009/0324761 A1 | 12/2009 | Khoo et al. |
| 2015/0361455 A1 | 12/2015 | Katz et al. |
| 2019/0375705 A1 | 12/2019 | Chae et al. |
| 2022/0062207 A1 | 3/2022 | Chae |
| 2022/0296542 A1 | 9/2022 | Chae |

FOREIGN PATENT DOCUMENTS

| CN | 107510706 | 12/2017 |
| EP | 1 671 534 | 6/2006 |
| GB | 2431876 | 5/2007 |
| JP | 2012-149004 | 8/2012 |
| JP | 5207341 B2 | 6/2013 |
| KR | 2005/0091116 | 9/2005 |
| KR | 2013-0104240 | 9/2013 |
| KR | 10-2014-0142580 | 12/2014 |
| KR | 10-2018-0075425 | 7/2018 |

(Continued)

OTHER PUBLICATIONS

Ramakrishna et al., "Influence of abiotic stress signals on secondary metabolites in plants," Plant Signal. Behav. Nov. 2011;6(11): 1720-31. PMID: 22041989. (Year: 2011).*
Ahn et al., Hepatocyte Nuclear Factor 4α in the Intestinal Epithelial Cells Protects Against Inflammatory Bowel Disease, Inflammatory Bowel Diseases, 14(7, pp. 908-920, (2008).
Al-Taweel et al., 2012, Bioactive Phenolic Amides from Celtis Africana, Molecules, 17:2675-2682.
Amaro et al., 2014, Hypoglycemic and hypotensive activity of a root extract of Smilax aristolochiifolia, standardized on N-trans-feruloyl-lyramine, Molecules, 19:11366-11384.
Amin et al., 2006, The Protective Effect of Tribulus terrestris in Diabetes, Ann. NY Acad. Sci 1084:391-401.
Appert et al., 1994, Structural and catalytic properties for the four phenylalanine ammonia-lyase isoenzymes from parsley (petroselinum crispum Nym.), Eur. J. Biochem. 225:491-499.
Ausubel et al., 1987, In Current Protocols in Molecular Biology, Wiley-Interscience (TOC).

(Continued)

*Primary Examiner* — Theodore R. Howell
(74) *Attorney, Agent, or Firm* — Knobbe, Martens, Olson & Bear, LLP

(57) ABSTRACT

This disclosure relates to methods and compositions with enhanced levels of one or more tyramine containing hydroxycinnamic acid amides. Also disclosed herein are methods for producing a consumable product with enhanced levels of a tyramine containing hydroxycinnamic acid amide. Some embodiments relate to a composition enriched with a tyramine containing hydroxycinnamic acid.

20 Claims, 6 Drawing Sheets

(56) References Cited

FOREIGN PATENT DOCUMENTS

| WO | WO 04/101757 | 11/2004 |
|----|----|----|
| WO | WO 08/154083 | 12/2008 |
| WO | WO 13/160811 | 10/2013 |
| WO | WO 18/161077 | 9/2018 |
| WO | WO 2019/140052 A1 | 7/2019 |

OTHER PUBLICATIONS

Babeu et al., 2014, Hepatocyte Nuclear Factor 4-Alpha Involvement in Liver and Intestinal Inflammatory Networks, World Journal of Gastroenterology, 20(1):22-30.
Baez-Viveros et al., 2004, Metabolic engineering and protein directed evoution increase the yield of L-phenylaianine synthesized from glucose in *Escherichia coli*, Biotechnol. Bioeng. 87:516-524.
Bandoni et al., 1968, Phenylalanine and tyrosine ammonia-lyase activity in some basidiomycetes, Phytochemistry 7: 205-207.
Becker et al., 1991, High-efficiency transformation of yeast by electroporation, in Guthrie ed., Methods in Enzymology, 194:186-187.
Berry, 1996, Improving production of aromatic compounds in *Escherichia coli* by metabolic engineering, Trends Biotechnol. 14:250-256.
Bongaerts et al., 2001, Metabolic engineering for microbial production of aromatic amino acids and derived compounds, Metab. Eng. 3:289-300.
Bradford, 1976, A rapid and sensitive method for the quantitation of microgram quantities of protein utilizing the principle of protein-dye binding, Anal. Biochem. 72:248-254.
Braus, Sep. 1991, Aromatic amino acid biosynthesis in the yeast *Saccharaomyces cerevisiae*: a model system for the regulation of a eukaryotic biosynthetic pathway, Microbiol Rev. 55:349-370.
Bruning et al., 2000, Role of Brain Insulin Receptor in Control of Body Weight and Reproduction, Science, 289:.2122-2125.
Brunt et al., 1999, Nonalcoholic Steatohepatitis: A Proposal for Grading and Staging the Histological Lesions, The American Journal of Gastroenterology, 94(9):2467-2474.
Butler et al., 2000, A Unique Metabolic Syndrome Causes Obesity in the Melanocortin-3 Receptor-Deficient Mouse, Endocrinology, 141(9):3518-3521.
Cai et al., 2006, Peptide deformylase is a potential target for anti-Helicobacter pylori drugs: Reverse docking, enzymatic assay, and X-ray crystallography validation, Protein Science, 15:2071-2081.
Cantos et al., 2000, Effect of postharvest ultraviolet irradiation on resveratrol and other phenolics on Cv. Napoleon table grapes, J. Agric. Food Chem. 48:4606-4612.
Carmiel-Haggai et al., 2005, A High-Fat Diet Leads to the Progression of Non-Alcoholic Fatty Liver Disease in Obese Rats, The FASEB Journal, 19(1):136-138.
Cattin et al., 2009, Hepatocyte Nuclear Factor 4α, a Key Factor for Homeostasis, Cell Architecture, and Barrier Function of the Adult Intestinal Epithelium, Molecular and Cellular Biology, 29(23):6294-6308.
Chahar et al., 2014, Chromatin Profiling Reveals Regulatory Network Shifts and a Protective Role for Hepatocyte Nuclear Factor 4α during Colitis, Molecular and Cellular Biology, 34(17):3291-3304.
Chatzigeorgiou et al. 2009, The Use of Animal Models in the Study of Diabetes Mellitus, In Vivo, 23:245-258.
Chen et al., 2000, Inactivation of the Mouse Melanocortin-3 Receptor Results in Increased Fat Mass and Reduced Lean Body Mass, Nature Genetics, 26(1):97-102.
Chen et al., Mar. 4, 2012, The isolation and identification of two compounds with predominant radical scavenging activity in hempseed, Food Chemistry, 134(2):1030-1037.
Chiba et al., 2003, Hepatocyte Nuclear Factor (HNF)-4alpha Triggers Formation of Functional Tight Junctions and Establishment of Polarized Epithelial Morphology in F9 Embryonal Carcinoma Cells, Experimental Cell Research, 286(2):288-297.

Chiba et al., 2006, The Nuclear Receptor Hepatocyte Nuclear Factor 4α Acts as a Morphogen to Induce the Formation of Microvilli, Journal of Cell Biology, 175(6):971-980.
Cho et al., Jan. 1, 2011, Study on the hypochlolesterolemic and antioxidative effects of tyramine derivatives from the root bark of Lycium chenes Miller, Nutrition Research and Practice, 5(5):412-420.
Choi et al., 2009, Increased production of S-adenysol-L-methionine using recombinant *Saccharomyces cerevisiae* sake K6, Korean J. Chem. Eng. 26(1):156-159.
Clegg et al., 2011, Consumption of a High-Fat Diet Induces Central Insulin Resistance Independent of Adiposity, Physiology & Behavior, 103(1):10-16.
Darsigny et al., 2009, Loss of Hepatocyte-Nuclear-Factor-4α Affects Colonic Ion Transport and Causes Chronic Inflammation Resembling Inflammatory Bowel Disease in Mice, PLoS One, 4(10):e7609.
Davison et al., 2017, Microbiota Regulate Intestinal Epithelial Gene Expression by Suppressing the Transcription Factor Hepatocyte Nuclear Factor 4 Alpha, Genome Research, 27:1195-1206.
Deaner et al., 2017, Systematic testing of enzyme perturbation sensitivities via graded dCas9 modulation in *Saccaromyces cerevisiae*, Metab. Eng. 40:14-22.
Deshpande, 1992, Ethanol production from cellulose by coupled saccharification/fermentaion using *Saccharomyces cerevisiae* and cellulase complex from Scherotium rolfsii UV-8 mutant, Appl. Biochem. Biotechnol., 36:227-234.
Douglas, 1996, Phenylpropanoid metabolism and lignin biosynthesis: from weeds to trees, Trends Plant Sci 1:171-178.
Drel et al., 2006, The Leptin-Deficient (ob/ob, Mouse: A New Animal Model of Peripheral Neuropathy of Type 2 Diabetes and Obesity, Diabetes, 55(12):3335-3343.
Ehlting et al., 1999, Three 4-coumarate:coenzyme A ligases in *Arabidopsis thaliana* represent two evolutionarily divergent classes in angiosperms, The Plant Journal 19(1):9-20.
Eichholz et al., 2011, UV-B-induced changes of volatile metabolites and phenolic compounds in blueberries (*Vaccimium corymbosum* L.), Food Chem. 126:60-64.
Emes et al., 1970, Partial purification and properties of L-phenylalanine ammonia-lyase from streptomyces verticillatus, Can. J. Biochem. 48:613-622.
Engels et al., 2018, Inhibition of Pro-Inflammatory Functions of Human Neutrophils by Constituents of Melodorum fruticosum Leaves, Chemistry & Biodiversity, 15:1-14.
Figlewicz et al., 1986, Brain Insulin Binding is Decreased in Wistar Kyoto Rats Carrying the 'fa' Gene, Peptides, 7(1):61-65.
Galanie et al., Sep. 4, 2015, Complete biosynthesis of opioids in yeast, Science, 349(6252):1095-1100.
Geisel et al., 2003, The Impact of Hyperhomocysteinemia as a Cardiovascular Risk Factor in the Prediction of Coronary Heart Disease, Clinical Chemistry and Laboratory Medicine, 41(11):1513-1517.
Gupta et al., 2005, The MODY1 Gene HNF-4alpha Regulates Selected Genes Involved in Insulin Secretion, Journal of Clinical Investigation, 115(4):1006-1015.
Hagel et al., 2005, Elevated tyrosine decarboxylase and tyramine hydroxycinnamoyltransferase levels increase wound-induced tyramine-derived hydroxycinnamioc acid amide accumulation in transgenic tobacco leaves, Planta, 221:904-914.
Hanson et al., 1981, Phenylalanine ammonia-Lyase, Biochem. Plants, 7:577-625.
Hanson et al., 1972, The enzymic elimination of ammonica, in The Enzymes (3rd ed., Boyer Ed., Academic: New York) pp. 75-167.
Hariri et al., 2010, High-Fat Diet-Induced Obesity in Animal Models, Nutrition Research Reviews, 23(2):270-299.
Havir et al., 1971, L-phenylalanine ammonia-ilase (Maize), Plant Physiol. 48:130-136.
Hayhurst et al., 2001, Hepatocyte Nuclear Factor 4α (Nuclear Receptor 2A1, Is Essential for Maintenance of Hepatic Gene Expression and Lipid Homeostasis. Molecular and Cellular Biology, 21(4):1393-1403.
Hodgins, May 10, 1971, Yeast phenylalanine ammonia-lyase, J. Biol. Chem. 246(9):2977-2985.

(56) References Cited

OTHER PUBLICATIONS

Hohlfeld et al., 1995, Partial purification and characterization of hydroxycinnamoyl-coenzyme a:tyramine hydroxycinnamoyltransferase from cell suspension cultures of solanum tuberosum, Plant Physiol. 107:545-552.
Hummel at al., 1972, The Influence of Genetic Background on Expression of Mutations at the Diabetes Locus in the Mouse. I. C57BL-KsJ and C57BL-6J Strains, Biochemical Genetics, 7(1):1-13.
Huszar et al., 1997, Targeted Disruption of the Melanocortin-4 Receptor Results in Obesity in Mice, Cell, 88(1):131-141.
Huyskens-Keil et al., 2007, UV-B induced changes of phenol composition and antioxidant activity in black currant fruit (*Ribes nigrum* L.), J. Appl. Bot. Food Qual. 81:140-144.
Ikeda et al., 2006, Towards bacterial strains overproducing L-tryptophan and other aromatics by metabolic engineering, Appl. Microbial. Biotechnol. 69:615-626.
Inoue et al., 2002, Defective Ureagenesis in Mice Carrying a Liver-specific Disruption of Hepatocyte Nuclear Factor 4α (HNF4α, HNF4α Regulates Ornithine Transcarbamylase In Vivo, The Journal of Biological Chemistry, 277:25257-252625.
Jiang et al., 2003, Expression and Localization of P1 Promoter-Driven Hepatocyte Nuclear Factor-4α (HNF4α, Isoforms in Human and Rats, Nuclear Receptor, 1:1-12.
Joost, 2010, The Genetic Basis of Obesity and Type 2 Diabetes: Lessons from the New Zealand Obese Mouse, a Polygenic Model of the Metabolic Syndrome, Results and Problems in Cell Differentiation, 52:1-11.
Kang et a., 2009, Production of plant-specific tyramine derivatives by dual expression of tyramine N-hydroxycinnamoyltransferase and 4-coumarate:coenzyme A ligase in *Escherichia coli*, Biotechnol Lett, 31:1469-1475.
Keller et al., 1996, Changes in the accumulation of soluble and cell wall-bound phenolics in elicitor-treated cell suspension cultures and fungus-infected leaves of solanum tuberosum, Phytochemistry 42:389-396.
Kennedy et al., 2010, Mouse Models of the Metabolic Syndrome, Disease Models & Mechanisms, 3(3-4):156-166.
Kikuchi et al., Feb. 1997, Mutational analysis of the feedback sites of phenylalanine-sensitive 3-Deoxy-d-arabino-heptulosonate-7-phosphate synthase of *Escherichia coli*, Appl. Environ. Microbiol. 630(2):761-762.
Kim et al., 2018, Portulaca oleracea extracts and their active compounds amerliorate imflammatory bowel diseases in vitor and in vivo by modulating TNF-α, IL-6 and IL-1β signalling, Food Research International, 106:335-343.
King et al., 2005, Characterization of Cross-Linked Hydroxycinnamic Acid Amides Isolated from Potato Common Scab Lesions, Phytochemistry, 66(20):2468-2473.
King, 2012, The Use of Animal Models in Diabetes Research, British Journal of Pharmacology, 166(3):877-894.
Kiselyuk et al., 2010, Phenothiazine neuroleptics signal to the human insulin promoter as evealed by a novel high-throughput screen, J Biomol. Screen 15(6):663-670.
Kiselyuk et al., 2012, HNF4α Antagonists Discovered by a High-Throughput Screen for Modulators of the Human Insulin Promoter, Chem Biol 19(7):806-818.
Kitahata et al., 1989, Production of Rubusoside Derivatives by Transgalactosylation of Various β-Galactosidases, Agricultural and Biological Chemistry, 53:.2923-2928.
Kleiner et al., 2005, Design and Validation of a Histological Scoring System for Nonalcoholic Fatty Liver Disease, Hepatology, 41(6):1313-1321.
Knobloch et al., 1977, 4-Coumarate:CoA ligase from cell suspension cultures of Petroselinum hortense Hoffm., Arch. Biochem. Biophys. 184:237-248.
Ko et al. 2015, N-trans-p-caffeoyl tyramine isolated from Tribulus terrestris exerts anti-inflammatory effects in lipopoiysaccharide-stimulated RAW 264.7 cells International Journal of Molecular Medicine, 36:1042-1048.

Koopman et al., 2012, Do novo production of the flavonoid naringenin in engineered *Saccharomyces cerevisiae*, Microb. Cell Fact. 11:155.
Koukol et al., Oct. 1961, The metabolism of aromatic compounds in higher plants, J. Biol. Chem. 236(10):2692-2698.
Lee et al., 1996, Two divergent members of a tobacco 4-coumarate:coenzyme A Ligase (4CL, gene family, Plant Physiol. 112:193-205.
Lee et al., 2013, Reversal of Lipotoxic Effects on the insulin Promoter by Alverine and Benfluorex: Identification as HNF4a Activators, ACS Chem Biol 8(8):1730-1736.
Lee et al., 2017, Anti-inflammatory effect of tribulusamide D isolated from Tribulus terrestris in lipopolysaccharide-stimulated RAW264.7 macrophages, Molecular Medicine Report, 16:4421-4428.
Lee et al., 2021, Liver fat storage is controlled by HNF4α through induction of lipophagy and is reversed by a potent HNF4α agonist Cell Death & Disease, 2021, 18 pages.
Leiter et al., 2004, Differential Levels of Diabetogenic Stress in Two New Mouse Models of Obesity and Type 2 Diabetes, Diabetes, 53(Suppl 1):S4-S11.
Leiter, 2009, Chapter 1: Selecting the Right Mouse Model for Metabolic Syndrome in Type 2 Diabetes Research: Methods in Molecular Biology, 560:1-17.
Leung et al., Aug. 1989, A method for random mutagenesis of a defined DNA segment using a modified polymerase chain reaction, Technique, 1 (1):11-15.
Levin et al., 1997, Selective Breeding for Diet-Induced Obesity and Resistance in Sprague-Dawley Rats, American Journal of Physiology, 273:R725-730.
Lobov et al., 1991, Enzymic Production of Sweet Stevioside Derivatives: Transglucosylation by glucosidases, Agricultural and Biological Chemistry, 55(12):2959-2965.
Lovdal et al., 2010, Synergetic effects of nitrogen depletion, temperature, and light on the content of phenolic compounds and gene expression in leaves of tomato, Phytochemistry 71:605-613.
Ludidi et al., May 15, 2015, The Intestinal Barrier in Irritable Bowel Syndrome: Subtype-Specific Effects of the Systemic Compartment in an in Vitro Model, PLoS One, 10(5):e0123498.
Ludwig et al., 1980, Nonalcoholic Steatohepatitis: Mayo Clinic Experiences With a Hitherto Unnamed Disease, Mayo Clinic Proceedings, 55(7):434-438.
Lutke-Eversloh et al., 2008, Combinatorial pathway analysis for improved L-tyrosine production in *Eschericia coli*: identification of enzymative bottlenecks by systematic gene overexpression, Metabolic Engineering 10:68-77.
Luttik et al., 2008, Alleviation of feedback inhibition in *Saccharomyces cerevisiae* aromatic amino acid biosynthesis: quantification of metabolic impact, Metab. Eng. 10:141-153.
Maciel et al., 2016, New Alcamide and Anti-oxidant Activity of Pilosocereus gounellei A, Weber ex K, Schum. Bly. Ex Rowl. (Cactaceae), Molecules, 21:1-13.
Macoy et al., 2015, Biotic stress related functions of hydroxycinnamic acid amide in plants, J. Plant Biol., 58:156-163.
Mao et al., 2017, Combinatorial analysis of enzymatic bottlenecks of L-tyrosine pathway by p-coumaric acid production in *Saccharamyces cerevisiae*, Biotechnol. Lett. 39(7):977-982.
Martinez-Jimenez et al., 2010, Hepatocyte Nuclear Factor 4α Coordinates a Transcription Factor Network Regulating Hepatic Fatty Acid Metabolism, Molecular and Cellular Biology, 30(3):565-577.
Matsuoka et al., 2015, Preserving Mafa Expression in Diabetic Islet β-cells Improves Glycemic Control in Vivo, Journal of Biological Chemistry, 290(12):7647-7657.
Millar et al., 2005, Determining hepatic Triglyceride Production in Mice:Comparison of Poloxamer 407 with Triton WR-1339, Journal of Lipid Research, 46:2023-2028.
Miller et al., 1987, Production of phenylalanine and organic acids by phosphoenolpyruvate carboxylase-dificient mutants of *Escherichia coli*, J. Ind. Microbiol. 2:143-149.
Mul et al., 2011, Melanocortin Receptor 4 Deficiency Affects Body Weight Regulation, Grooming Behavior, and Substrate Preference in the Rat, Obesity, 20(3):612-621.

(56) References Cited

OTHER PUBLICATIONS

Negrel et al., 1993, Wound-induced tyramine hydroxycinnamoyl transferase in potato (*Solanum tuberosum*) tuber discs, J. Plant Physiol. 142(5):518-524.
Negrel et al., 1995, Induction of phenylpropanoid and tyramine metabolism in pectinase- or pronase-elicited cell suspension cultures of tobacco (*Nicotiana tabacum*), Physiol. Plant. 95:569-574.
Nelms et al., Aug. 1992, Novel mutations in the pheA gene of *Escherichia coli* K-12 which result in highly feedback inhibition-resistant variants of chorismite mutase/prephenate dehydratase, Appl. Environ. Microbiol. 58(8):2592-2598.
Neuschwander-Tetri et al., 2003, Nonalcoholic Steatohepatitis: Summary of an AASLD Single Topic Conference, Hepatology, 37(5):1202-1219.
Nijkamp et al., 2005, The solvent-tolerant Pseudomonas putida S12 as host for the production of cinnamic acid from glucose, Appl. Microbiol. Biotechnol. 69:170-177.
Nijkamp et al., 2007, Optimization of the solvent-tolerant Pseudomonas putida S12 as host for the production of p-coumarate from glucose, Appl. Microbiol. Biotechnol. 74:617-624.
Nishioka et al., 1997, Isolation and activity of N-p-coumaroyltyramine, an a-Jlucosidase inhibitor in welsh onion (*Allium fislulosum*), Biosci. Biotechnol. Biochem. 61(7):1138-1141.
Ogata et al., 1967, Metabolism of aromatic amino acid in microorganisms, Agric. Biol. Chem. 31(2):200-206.
Okayasu et al., 1990, A Novel Method in the Induction of Reliable Experimental Acute and Chronic Ulcerative Colitis In Mice, Gastroenterology, 98(3):694-702.
Olson et al., 2007, Production of tyrosine from sucrose or glucose achieved by rapid genetic changes to phenylalanine-producing *Escherichia coli* strains, Appl. Microbiol. Biotechnol. 74(5):1031-1040.
Palva et al., 1984, IacZ fusions to genes that specify exported proteins: a general technique, Nol. Gen Genet, 194:388-394.
Park et al., 2009, Endosperm-specific expression of tyramine N-hyroxycinnamoyltransferase and tyrosine decarboxylase from a single self-processing polypeptide produces high levels of tyramine derivatives in rice seeds, Biotechnol. Lett. 31(6):911-915.
Park, 2007, Caffedymine from cocoa has cox inhibitory activity suppressing the expression of a platelet activation marker, P-selectin, J. Agric. Food Chem, 55:2171-2175.
Parviz et al., 2003, Hepatocyte Nuclear Factor 4alpha Controls the Development of a Hepatic Epithelium and Liver Morphogenesis, Nature Genetics, 34(3):292-296.
Patnaik et al., Nov. 1994, Engineering of *Escherichia coli* central metabolism for aromatic metabolite production with near theoretical yield, Appl. Environ. Microbiol., 60(11):3903-3908.
Peddibhotla et al., 2013, Discovery of ML314, a Brain Penetrant Nonpeptidic β-Arrestin Biased Agonist of the Neurotensin NTR1 Receptor, ACS Medicinal Chemistry Letters, 4(9):pp. 846-851.
Porter et al., 1999, Functional characterization of agonists at recombinant human 5-HT2A, 5-HT2B and 5-HT2C receptors in CHO-K1 cells, Br J. Pharmacol. 128(1):13-20.
PubChem-CID-88222313, Create Date: Feb. 12, 2015, 9 pp.
PubChem-pocompound-CID 54408305, Create Date Dec. 4, 2011, pp. 1-24.
PubChem-pccompound-selected items 1-14, Create Date Mar. 26, 2005 to Aug. 6, 2016, 3 pp.
Qin et al., 2018, An obesity-associated gut microbiome reprograms the intestinal epigenome and leads to altered colonic gene expression, Genome Biol. 19:7.
Rodriguez et al., 2015, Establishment of a yeast platform strain for production of p-coumaric acid through metabolic enGineering of aromatic amino acid biosynthsis, MetAbolic Engineering, 31:181-188.
Rogers et al., 1984, Meal Patterns and Food Selection During the Development of Obesity in Rats Fed a Cafeteria Diet, Neuroscience & Biobehavioral Reviews, 8(4):441-453.

Roje et al., Feb. 8, 2002, Metabolic engineering in yeast demonstrates that S-adenosyimethionine controls flux through the methylenetetrahydrofolate reductase reaction in vivo, J. Biol. Chem. 277:4056-4061.
Rosler et al., 1997, Maise phenylalanine ammonia-lyase has tyrosine ammonia-lyase activity, Plant Physiol. 113:175-179.
Sambrook et al., 1989, Molecular Cloning: A Laboratory Manual, 2nd ed., Cold Spring Harbor Laboratory, Cold Spring Harbor, NY (TOC).
Sanders et al., 2016, De Novo Lipogenesis in the Liver in Health and Disease: More Than just a Shunting Yard for Glucose, Biological reviews of the Cambridge Philosophical Society, 91(2):452-468.
Savage, 2009, Mouse Models of Inherited Lipodystrophy, Disease Models & Mechanisms, 2(11-12):554-562, (2009).
Schmidt et al., 1998, Elicitor-stimulated biosynthesis of hydroxycinnamoyltyramines in cell suspension cultures of Solanum tuberosum, Planta, 205:51-55.
Schmidt et al., Feb. 12, 1999, Cloning and expression of a potato cDNA encoding hydroxycinnamoyl-CoA:Tyramine N-(Hydroxycinnamoyl)transferase, J. Biol. Chem. 274(7):4273-4280.
Schmidt et al., Mar. 21, 2014, Assessment of constituents inAlliumby multivarate data analysis, high-resolution α-glucosidase inhibition assay and HPLC-SPE, Food Chemistry, 161:192-198.
Shepherd et al., 1993, Adipose Cell Hyperplasia and Enhanced Glucose Disposal in Transgenic Mice Overexpressing GLUT4 Selectively in Adipose Tissue, Journal of Biological Chemistry, 268:.22243-22246.
Shiota et al., 2012, Diabetes in Zucker Diabetic Fatty Rat, Methods in Molecular Biology, 933:103-123.
Sim et al., 2015, Bacterial synthesis of N-hydroxycinnamoyl phenethylamines and tyramines, Microbial Cell Fact. 14:162.
Spath et al., 1998, Hepatocyte Nuclear Factor 4 Provokes Expression of Epithelial Marker Genes, Acting As a Morphogen in Dedifferentiated Hepatoma Cells, Journal of Cell Biology, 140(4):935-946.
Spee et al., 1993, Efficient random mutagenesis method with adjustable mutation frequency by use of PCR and dITP, Nucl. Acids Res. 21(3):777-778.
Sprenger et al., 2007, From scratch to value: engineering *Escherichia coli* wild type cells to the production of L-phenylalanine and other fine chemicals derived from chorismate, Appl. Microbial. Biotechnol. 75:739-749.
Stenman et al., 2012, High-Fat-Induced Intestinal Permeability Dysfunction Associated with Altered Fecal Bile Acids, World Journal of Gastroenterology, 18(9):923-929.
Tatarko et al., 2001, Disruption of a global regulatory gene to enhance central carbon flux into phenylalanine biosynthesis in *Escherichia coli*, Curr. Microbiol. 43:26-32.
Traini et al., 2016, Changes of Excitatory and inhibitory Neurotransmitters in the Colon of Rats Underwent to the Wrap Partial Restraint Stress, Neurogastroenterology & Motility, 28(8):1172-1185.
Traini et al., 2017, Repeated Otilonium Bromide Administration Prevents Neurotransmitter Changes in Colon of Rats Underwent to Wrap Restraint Stress, Journal of Cellular and Molecular Medicine, 21:735-745.
Trenchard et al., 2015, De novo production of the key branch point benzyilsoquinoline alkaloid reticuline in yeast, Metab. Eng. 31:74-83.
Tschop et al., 2001, Rodent Obesity Models: An Overview, Experimental and Clinical Endocrinology & Diabetes, 109(6)307-319.
Villegas et al., 1990, Elicitor-induced hydroxycinnamoyl-CoA:tyramine hydroxycinnamoyltransferase in plant cell suspension cultures, Physiol. Plant. 78:414-420.
Wang et al., 2014, Leptin- and Leptin Receptor-Deficient Rodent Models: Relevance for Human Type 2 Diabetes, Current Diabetes Reports, 10(2):131-145.
Wang et al., 2017, Identification and Quantification of Potential Anti-inflammatory Hydroxycinnamic Acid Amides from Wolfberry, Journal of Agricultural and Food Chemistry, 65:364-372.
Wang et al., Mar. 25, 1994, Functional characterization of a unique liver gene promoter, J. Biol. Chem. 269(12):9137-9146.

(56) References Cited

OTHER PUBLICATIONS

Williams et at., 1988, Stress-Induced Changes in Intestinal Transit in the Rat: A Model for Irritable Bowel Syndrome, Gastroenterology, 94(3):611-621.
Yakandawala et al., 2008, Metabolic engineering of *Escherichia coli* to enhance phenylalanine production, Appl. Microbiol. Biotechnol. 78:283-291.
Yamamoto et al., 1994, Effective Production of Glycosyl-Steviosides by Alpha-1,6 Transglucosylation of Dextrin Dextranase, Bioscience, Biotechnology, and Biochemistry, 58(9):1657-1661.
Yaswen et al., 1999, Obesity in the Mouse Model of Pro-Opiomelanocortln Deficiency Responds to Peripheral Melanocortin, Nature Medicine, 5(9):1066-1070.
Yeh, Aug. 2004, C-reactive Protein is an Essential Aspect of Cardiovascular Risk Factor Stratification, The Canadian Journal of Cardiology, 20(Suppl B):93B-96B.
Yi et al., 2003, Altered glucose transport and shikimate pathway product yields in *E. coli*, Biotechnol. Prog. 19:1450-1459.
Yin et al., Hepatic HNF4α Is Essential for Maintaining Triglyceride and Cholesterol Homeostasis, Arteriosclerosis, Thrombosis, and Vascular Biology, 31(2, pp. 328-336, (2011).
Zacares et al., 2007, Induction of p-Coumaroyldopamine and feruloyldopamine, two novel metabolites, in tomato by the bacterial pathogen Pseudomonas syringae, Mol. Plant Microbe Interact. 20(11):1439-1448.
Zhao et al., Feb. 1994, Pseudomonas aeruginosa possesses homologues of mammalian phenylalanine hydroxylase and 4α-carbinolamine dehydratase/DCoH as part of a three-component gene cluster, Proc. Natl. Acad. Sci. USA. 91:1366-1370.
Zhou et al., 1991, Random mutagenesis of gene-sized DNA molecules by use of PCR with Taq DNA polymerase, Nucleic Acids Res. 19(21):6052-6052.
Back et al. 'Cloning and Characterization of a Hydroxycinnamoyl-CoA: Tyramine N-(hydroxycinnamoyl) transferase Induced Response to UV-C and Wounding from Capsicum annuum', Plant Cell Physiol. 2001, vol. 42(5), pp. 475-481. abstract; p. 476, col. 1, para 2.
Ishihara et al. 'Induction of N-hydroxycinnamoyltyramine Synthesis and Tyramine N-Hydroxycinnamoyltransferase (THT) Activity by Wounding in Maize Leaves', BioSci. Biotechnol. Biochem., 2000, vol. 64(5), pp. 1025-1031. abstract; p. 1025, col. 2, para 3; p. 1026, col. 1, para 3; p. 1027, col. 2, para 3, Figures 1b and 2; p. 1028, col. 2, para 3, Table 3; p. 1029, col. 1, para 3 to col. 2, para 1, Table 4.
Pang et al. 'Polyamines, All-purpose Players in Response to Environment Stresses in Plants', Plant Stress, 2007, vol. 1(2), pp. 173-188. abstract; p. 177, col. 2, para 5; p. 175, col. 1, para 3.
International Search Report and Written Opinion, dated Jan. 29, 2021, 15 pages.

\* cited by examiner

EXTRACT, CONSUMABLE PRODUCT AND METHOD FOR ENRICHING BIOACTIVE METABOLITE IN AN EXTRACT

RELATED APPLICATIONS

This application is a continuation of PCT/US2020/059726 filed Nov. 9, 2020, which claims the priority benefit of U.S. Provisional Application No. 62/933,660, filed Nov. 11, 2019, the entire content of each of which is hereby incorporated by reference herein in its entirety.

BACKGROUND

N-Hydroxycinnamic acid amides (HCAAs) are synthesized by the condensation of hydroxycinnamoyl-CoA thioesters and aromatic amines. The hydroxycinnamoyl-CoA thioesters include cinnamoyl-CoA, p-coumaroyl-CoA, caffeoyl-CoA, feruloyl-CoA, and sinapoyl-CoA, and are synthesized from cinnamic acid by a series of enzymes, including cinnamate-4-hydroxylase, coumarate-3-hydroxylase, caffeic acid O-methyltransferase, ferulate-5-hydroxylase, and hydroxycinnamate:CoA ligase (Douglas (1996) *Trends Plant Sci* 1:171-178).

Tyramine-derived HCAAs are commonly associated with the cell wall of tissues near pathogen-infected or wound healing regions. Moreover, feruloyltyramine and feruloyloctapamine are covalent cell wall constituents of both natural and wound periderms of potato (*Solanum tuberosum*) tubers, and are putative components of the aromatic domain of suberin. The deposition of HCAAs is thought to create a barrier against pathogens by reducing cell wall digestibility. HCAAs are formed by the condensation of hydroxycinnamoyl-CoA thioesters with phenylethylamines such as tyramine, or polyamines such as putrescine. The ultimate step in tyramine-derived HCAA biosynthesis is catalyzed by hydroxycinnamoyl-CoA:tyramine N-(hydroxycinnamoyl) transferase. In view of the important role of these compounds, it is desirable to have a means and methods that are capable of increasing the levels of these secondary metabolites in plants.

EP 1671534 A1 describes a method of increasing the content of depsides, preferably dicaffeoylquinic acids and/or dicaffeoyltartaric acids in a plant by treating the plant with biotic and/or abiotic stimuli.

U.S. Pat. No. 7,666,455 teaches a method for increasing the amount of resveratrol in a peanut material by size-reducing the peanut kernel, abiotically stressing the size-reduced peanut kernel, and incubating the abiotically stressed size-reduced peanut kernel under conditions capable of increasing the amount of resveratrol in the size-reduced peanut kernel.

U.S. Pat. No. 9,227,898 describes a method for increasing stilbene production, particularly resveratrol and piceatannol, in sugarcane by irradiating cut sides of sugarcane billets with Ultraviolet-C or Ultraviolet-B light.

US 2004/0234657 A1 teaches the treatment of a plant with a modified lecithin, e.g., enzyme-modified lecithin (EML) and chemically modified lecithin such as acetylated lecithin (ACL) and hydroxylated lecithin (HDL), to induce expression of phenylalanine ammonia lyase, polyphenol oxidase, and peroxidase, and enhance lignin production.

Further, wounded tobacco (Hagel, & Facchini (2005) *Plan ta* 221:904-914) and potato tuber discs (Negrel, et al. (1993) *J. Plant Physiol.* 142(5):518-524) have been shown to produce increased levels of amides of ferulic acid with tyramine or octopamine, and elicitor chitosan treatment has been shown in increase coumaroyl tyramine in potato (Schmidt, et al. (1999) *J. Biol. Chem.* 274:4273-4280).

SUMMARY OF THE DISCLOSURE

In aspects, the disclosure provided herein describes methods for producing a consumable product with enhanced levels of a tyramine containing hydroxycinnamic acid amide. In some embodiments, the method for producing a consumable product with enhanced levels of a tyramine containing hydroxycinnamic acid amide, comprising:

(a) subjecting a plant for producing a compound of Formula I

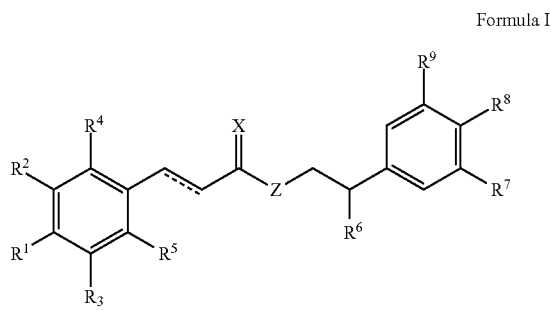

Formula I wherein $R^1$, $R^2$, $R^3$, $R^4$, $R^5$, $R^6$, $R^7$, $R^8$, and $R^9$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl; the dashed bond is present or absent;

X is $CH_2$ or O;

Z is $CHR^a$, $NR^a$, or O; and $R^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl, the dashed bond is present or absent, to at least one biotic or abiotic stress; and (b) incorporating the plant or extract into a consumable product.

In some embodiments, the method for producing a consumable product with enhanced levels of a tyramine containing hydroxycinnamic acid amide, comprising:

(a) subjecting a plant for producing a compound of Formula II

Formula II

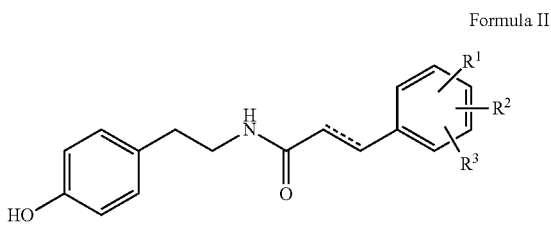

wherein

R¹, R², and R³ are each independently present or absent, and when present is a substituent on one or more ring atoms (e.g., position 2, 3, and/or 4) and is for each ring atom independently a hydroxy group, halo group, substituted or unsubstituted lower alkyl group, or substituted or unsubstituted lower alkoxy group, the dashed bond is present or absent, to at least one biotic or abiotic stress; and (b) incorporating the plant or extract into a consumable product.

In some embodiments, the method further comprising recovering an extract from the plant. In some embodiments, the method further comprising contacting the plant with a precursor of a tyramine containing hydroxycinnamic acid amide. In some embodiments, the biotic stress is false germination. In some embodiments, the at least one biotic or abiotic stress is applied post-harvest. In some embodiments, the at least one biotic or abiotic stress is applied pre-harvest. In some embodiments, the abiotic stress is selected from at least one of hyperosmotic stress, salt, temperature stresses, aberrant nutrient conditions, mechanical shock flooding, wounding, anaerobic stress, oxidative stress, ozone, high light, heavy metals, toxic chemicals, ultrasound, ultraviolet light, elicitor chitosan treatment, modified lecithin treatment, or abscisic acid treatment.

In some embodiments, the optionally recovering an extract from the plant comprises an ethanol extract. In some embodiments, the plant is selected from at least one of *Tribulus terrestris, Annona montana, Annona muricata, Annona cherimola, Annona atemoya, Solanum tuberosum, Cannabis sativa, Lycium barbarum, Allium sativum, Solanum lycopersicum, Capsicum annuum, Capsicum frutescens, Solanum tuberosum, Annona* spp., *Lycium barbarum, Ipomoea batatas, Zea Mays, Piper nigrum, Dysphania ambrosioides, Hibiscus sabdariffa, Piper auritum, Solanum lycopersicum*, or *Allium fistulosum*.

In some embodiments, the compound is selected from p-coumaroyltyramine, n-caffeoyltyramine, n-feruloyltyramine, and sinpoyltyramine. In some embodiments, the n-feruloyltyramine yield is greater than 1000 mg/kg of the plant. In some embodiments, the p-coumaroyltyramine yield is greater than 50 mg/kg of the plant. In some embodiments, the at least one biotic or abiotic stress comprises incubating the plant at about 25° C. to about 37° C. and a pH of 6.5 to about 9.5. In some embodiments, the at least one biotic or abiotic stress comprises incubating the plant at about 30° C. and a pH of about 8.5.

In some embodiments, the abiotic stress is physical wounding and the compound of Formula I is n-feruoyltyramine. In some embodiments, the physical wounding increases n-feruloyltyramine is increased by at least 9-fold. In some embodiments, the physical wounding increases n-feruloyltyramine is increased by at least 13-fold. In some embodiments, the physical wounding increases n-feruloyltyramine is increased by at least 33-fold. In some embodiments, the abiotic stress is ultraviolet light and the compound of Formula I is n-feruloyltyramine, n-caffeoyltyramine, and p-coumaroyltyramine. In some embodiments, the plant is exposed to ultraviolet light for about 15 to about 30 minutes. In some embodiments, the abiotic stress is temperature stresses and the compound of Formula I is n-feruloyltyramine, n-caffeoyltyramine, and p-coumaroyltryamine. In some embodiments, the temperatures stress increases the production of n-feruloyltyramine, n-caffeoyltyramine, and p-coumaroyltryamine from about 25% to about 47%.

In some embodiments, a consumable product is produced by the method as described herein. In some embodiments, the consumable product is a dietary supplement, food ingredient, food additive, food product, feed product, a medical food, nutraceutical or pharmaceutical composition.

Some embodiments relate to a composition enriched for a tyramine containing hydroxycinnamic acid amide comprising, an extract or source material including one or more precursors of a tyramine containing hydroxycinnamic acid amide, wherein the extract or source material has been contacted with an enzymatic material, wherein the enzymatic material comprises one or more endogenous enzymes capable of converting the one or more precursors to the tyramine containing hydroxycinnamic acid amide.

In some embodiments, the enzymatic material comprises a phenylalanine ammonia lyase, 4-courmarate-CoA ligase, cinnamate-4-hydroxylase, coumarate-3-hydroxylase, coumaroyl-CoA 3-hydroxylase, caffeoyl-CoA O-methyltransferase, ferulate-5-hydroxylase, caffeic acid/5-hydroxyferulic acid O-methyltransferase, tyrosine ammonia lyase, or a combination thereof. In some embodiments, the tyramine containing hydroxycinnamic acid amide is N-caffeoyltyramine, N-feruloyltyramine, 5-hydroxyferuloyltyramine, p-coumaroyltyramine, cinnamoyltyramine, sinapoyltyramine, or a combination thereof. In some embodiments, the composition is a consumable product. In some embodiments, the consumable product is a dietary supplement, food ingredient, food additive, feed product, food product, a medical food, nutraceutical or pharmaceutical composition.

In some embodiments, a method for enhancing levels of a tyramine containing hydroxycinnamic acid amide in an extract or source material is provided herein. In some embodiments, the method comprises contacting an extract or source material including one or more precursors of a tyramine containing hydroxycinnamic acid amide with an enzymatic material, wherein the enzymatic material comprises one or more endogenous enzymes capable of converting the one or more precursors to the tyramine containing hydroxycinnamic acid amide, thereby enhancing the levels of a tyramine containing hydroxycinnamic acid amide in the extract or source material. In some embodiments, the method further comprises contacting the extract or source material with a precursor of a tyramine containing hydroxycinnamic acid amide. In some embodiments, the tyramine containing hydroxycinnamic acid amide is a compound of Formula I. In some embodiments, the source materials is selected from at least one of *Tribulus terrestris, Annona montana, Annona muricata, Annona cherimola, Annona atemoya, Solanum tuberosum, Cannabis sativa, Lycium barbarum, Allium sativum, Solanum lycopersicum, Capsicum annuum, Capsicum frutescens, Solanum tuberosum, Annona* spp., *Lycium barbarum, Ipomoea batatas, Zea Mays, Piper nigrum, Dysphania ambrosioides, Hibiscus sabdariffa, Piper auritum, Solanum lycopersicum*, or *Allium fistulosum*.

This disclosure also provides a composition enriched for a tyramine containing hydroxycinnamic acid amide composed of an extract including one or more precursors of a tyramine containing hydroxycinnamic acid amide, wherein said extract has been contacted with an enzymatic material including one or more endogenous enzymatic activities that convert the one or more precursors to the tyramine containing hydroxycinnamic acid amide. In some embodiments, the enzymatic material comprises a phenylalanine ammonia lyase, 4-courmarate-CoA ligase, cinnamate-4-hydroxylase, coumarate-3-hydroxylase, coumaroyl-CoA 3-hydroxylase, caffeoyl-CoA O-methyltransferase, ferulate-5-hydroxylase, caffeic acid/5-hydroxyferulic acid O-methyltransferase, tyrosine ammonia lyase, or a combination thereof. In other embodiments, the tyramine containing hydroxycinnamic acid amide is N-caffeoyltyramine, N-feruloyltyramine, 5-hydroxyferuloyltyramine, p-coumaroyltyramine, cinnamoyltyramine or sinapoyltyramine. A consumable product, e.g., a dietary supplement, food ingredient or additive, food product, a medical food, nutraceutical or pharmaceutical composition is also provided, as is a method for enhancing levels of a tyramine containing hydroxycinnamic acid amide in an extract.

DETAILED DESCRIPTION OF THE DISCLOSURE

Figure 1:
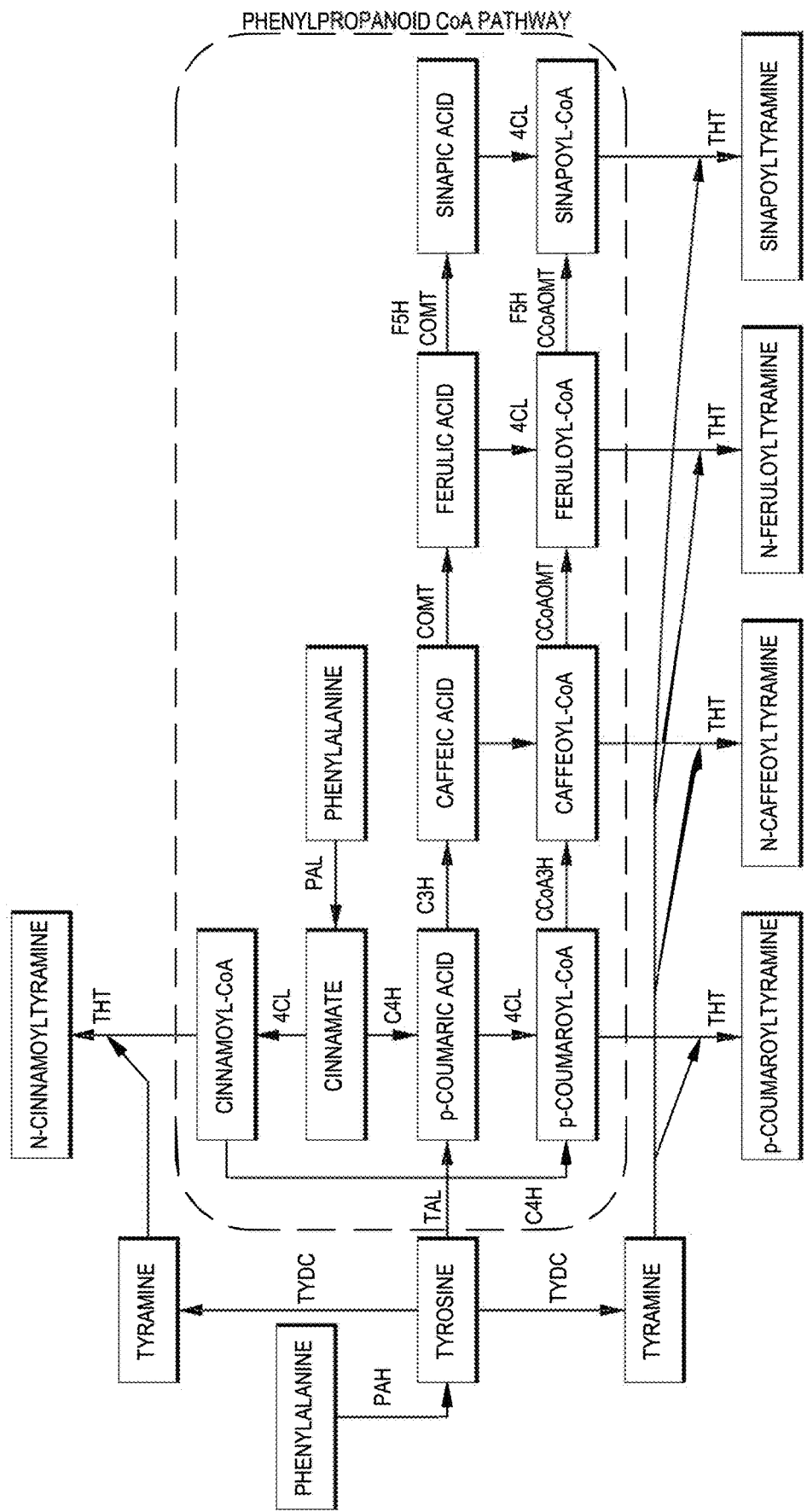
FIG. 1 depicts a schematic pathway for the biosynthesis of tyramine containing hydroxycinnamic acid amides from hydroxycinnamoyl-CoA esters and tyramine. However, cofactors and co-substrates are not shown for clarity. Enzymes of the phenylpropanoid pathway are phenylalanine ammonia-lyase (PAL, E.C. 4.3.1.24); cinnamate-4-hydroxylase (C4H, E.C. 1.14.14.91); 4-coumaroyl-CoA ligase (4CL, E.C. 6.2.1.12); coumarate-3-hydroxylase (C3H, E.C. 1.14.13.-); coumaroyl-CoA 3-hydroxylase (CCoA3H, or 5-O-(4-coumaroyl)-D-quinate 3'-monooxygenase, E.C. 1.14.14.96); caffeoyl-CoA O-methyltransferase (CCoA-OMT, E.C. 2.1.1.104); ferulate-5-hydroxylase (F5H, E.C. 1.14.-.-); and caffeic acid/5-hydroxyferulic acid O-methyltransferase (COMT, E.C. 2.1.1.68). Additional enzymes in the biosynthesis of tyramine containing hydroxycinnamic acid amides include hydroxycinnamoyl CoA:tyramine hydroxycinnamoyltransferase (THT, E.C. 2.3.1.110); tyrosine ammonia lyase (TAL, E.C. 4.3.1.23), phenylalanine hydroxylase (PAH, E.C. 1.14.16.1) and tyrosine decarboxylase (TYDC, E.C. 4.1.1.25).

Tyramine-derived N-hydroxycinnamic acid amides (HCAAs) are commonly associated with the cell wall of tissues near pathogen-infected or wound healing regions of plants. Moreover, feruloyltyramine and feruloyloctapamine are covalent cell wall constituents of both natural and wound periderms of potato (*Solanum tuberosum*) tubers. The deposition of HCAAs is thought to create a barrier against pathogens by reducing cell wall digestibility.

Tyramine containing hydroxycinnamic acid amides have now been shown to exhibit agonistic activity toward HNF4α (hepatocyte nuclear factor 4α), a global nuclear transcription factor that regulates expression of genes involved in maintaining balanced metabolism (homeostasis). By agonizing HNF4α activity, the plant-specific tyramine derivatives find use in mitigating the adverse effects of free fatty acids, modulating metabolism, improving digestive health and addressing the underlying pathogenesis of metabolic disorders, such as nonalcoholic fatty liver disease, nonalcoholic steatohepatitis and type II diabetes mellitus.

Accordingly, the present disclosure provides compositions with enhanced levels of one or more tyramine containing hydroxycinnamic acid amides. In some embodiments, the compositions are prepared by contacting an extract including one or more precursors of a tyramine containing hydroxycinnamic acid amide with an enzymatic material including one or more endogenous enzymatic activities that convert the one or more precursors to the tyramine containing hydroxycinnamic acid amide. Alternatively, or in addition to, enhanced levels of a tyramine containing hydroxycinnamic acid amide can be achieved by subjecting a plant to at least one biotic or abiotic stress, optionally recovering an extract from the plant; and incorporating the plant or extract into a consumable product. The present in situ methods allow for increased yield of tyramine containing hydroxycinnamic acid amides in plant extracts or fractions thereof thereby reducing downstream processing and purification costs.

In some aspects, a tyramine containing hydroxycinnamic acid amide has the structure of Formula I and includes homodimers, heterodimers, and conjugates thereof:

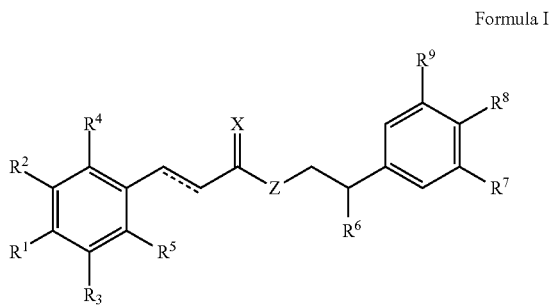

Formula I

In some embodiments, $R^1$, $R^2$, $R^3$, $R^4$, $R^5$, $R^6$, $R^7$, $R^8$, and $R^9$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl.

In some embodiments, $R^1$, $R^2$, $R^3$, and $R^8$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$ alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$ heterocyclyl, optionally substituted —(O)$C_{1-6}$alkyl$C_{4-12}$ heterocyclyl, optionally substituted —(O)$C_{4-12}$ aryl, optionally substituted —(O)$C_{1-6}$alkyl$C_{5-12}$ aryl, optionally substituted —(O)$C_{1-12}$ heteroaryl, and optionally substituted —(O)$C_{1-6}$alkyl$C_{1-12}$ heteroaryl, and $R^4$, $R^5$, $R^6$, $R^7$, and $R^9$ are each independently hydrogen, deuterium, hydroxyl, or halogen;

In some embodiments, $R^1$, $R^2$, and $R^8$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$ alkynl, optionally substituted, —(O)$C_{4-12}$ cycloalkyl, optionally substituted —(O)$C_{1-6}$alkyl$C_{4-12}$ cycloalkyl, optionally substituted —(O)$C_{4-12}$ heterocyclyl, optionally substituted —(O)$C_{1-6}$alkyl$C_{4-12}$ heterocyclyl, optionally substituted —(O)$C_{4-12}$aryl, optionally substituted —(O)$C_{1-6}$alkyl$C_{5-12}$aryl, optionally substituted —(O)$C_{1-12}$ heteroaryl, and optionally substituted —(O)$C_{1-6}$alkyl$C_{1-12}$ heteroaryl, and $R^3$, $R^4$, $R^5$, $R^6$, $R^7$, and $R^9$ are each independently hydrogen, deuterium, hydroxyl, or halogen.

In some embodiments, the dashed bond is present or absent.

In some embodiments, X is $CH_2$ or O.

In some embodiments, Z is $CHR^a$, $NR^a$, or O.

In some embodiments, $R^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$ cycloalkyl, optionally substituted —(O)$C_{1-6}$alkyl$C_{4-12}$ cycloalkyl, optionally substituted —(O)$C_{4-12}$ heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$ heteroaryl, and optionally substituted —(O)$C_{1-6}$alkyl$C_{1-12}$heteroaryl.

In some embodiments, a tyramine containing hydroxycinnamic acid amide has the structure of Formula II and includes homodimers, heterodimers, and conjugates thereof (for example lignanamides),

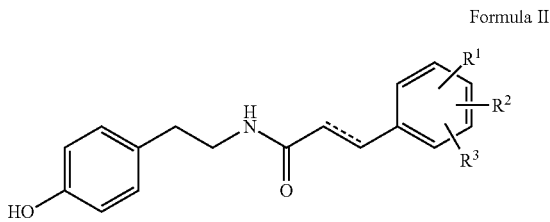

Formula II wherein $R^1$ is present or absent, and when present is a substituent on one or more ring atoms (e.g., position 2, 3, and/or 4) and is for each ring atom independently a hydroxy group, halo group, substituted or unsubstituted lower alkyl group, or substituted or unsubstituted lower alkoxy group; $R^2$ is present or absent, and when present is a substituent on one or more ring atoms (e.g., position 2, 3, and/or 4) and is for each ring atom independently a hydroxy group, halo group, substituted or unsubstituted lower alkyl group, or substituted or unsubstituted lower alkoxy group, $R^3$ is present or absent, and when present is a substituent on one or more ring atoms (e.g., position 2, 3, and/or 4) and is for each ring atom independently a hydroxy group, halo group, substituted or unsubstituted lower alkyl group, or substituted or unsubstituted lower alkoxy group, and the dashed bond is present or absent. In accordance with this disclosure, a tyramine containing hydroxycinnamic acid amide includes both cis and trans isomers.

For the groups herein, the following parenthetical subscripts further define the groups as follows: "$(C_n)$" defines the exact number (n) of carbon atoms in the group. For example, "$C_1$-$C_{16}$-alkyl" designates those alkyl groups having from 1 to 6 carbon atoms (e.g., 1, 2, 3, 4, 5, or 6, or any range derivable therein (e.g., 3-6 carbon atoms)).

The term "lower alkyl" is intended to mean a branched or unbranched saturated monovalent hydrocarbon radical containing 1 to 6 carbon atoms (i.e., $C_1$-$C_6$-alkyl), such as methyl, ethyl, propyl, isopropyl, tert-butyl, butyl, n-hexyl and the like.

Similarly, a lower alkoxy group is a $C_1$-$C_6$-alkoxy group having the structure —OR wherein R is "alkyl" as defined further above. Particular alkoxy groups include, by way of example, methoxy, ethoxy, n-propoxy, isopropoxy, n-butoxy, tert-butoxy, iso-butoxy, sec-butoxy, n-pentoxy, 1,2-dimethylbutoxy, and the like.

The term "halo" is used herein to refer to chloro (Cl), fluoro (F), bromo (Br) and iodo (I) groups. In some embodiments, the halo group is a fluoro group.

In any of the groups described herein, a substituted group (e.g., a substituted lower alkyl group or substituted lower alkoxy group) refers to an available hydrogen being replaced with an alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, halo, nitro, cyano, carboxy, aralkoxycarbonyl, heteroarylsulfonyl, alkoxycarbonyl, alkylsulfonyl, alkylthio, arylthio, aryloxycarbonyl, arylsulfonyl, heteroarylthio, aralkylthio, heteroaralkylthio, cycloalkyl, heterocyclyl or glycosyl group.

In some embodiments, the disclosure encloses a compound of Formula (III):

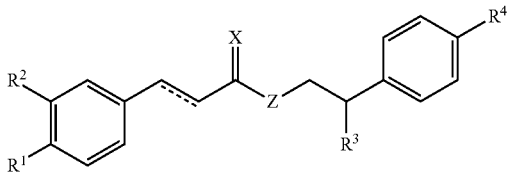

Formula (III)

In some embodiments, $R^1$, $R^2$, $R^3$, and $R^4$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$ alkynl, optionally substituted, —(O)$C_{4-12}$ cycloalkyl, optionally substituted —(O)$C_{1-6}$alkyl$C_{4-12}$ cycloalkyl, optionally substituted —(O)$C_{4-12}$ heterocyclyl, optionally substituted —(O)$C_{1-6}$alkyl$C_{4-12}$ heterocyclyl, optionally substituted —(O)$C_{4-12}$aryl, optionally substituted —(O)$C_{1-6}$alkyl $C_{5-12}$aryl, optionally substituted —(O)$C_{1-12}$ heteroaryl, and optionally substituted —(O)$C_{1-6}$alkyl$C_{1-12}$ heteroaryl.

In some embodiments, the dashed bond is present or absent.

In some embodiments, Z is $CHR^a$, $NR^a$, or O.

In some embodiments, $R^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$ cycloalkyl, optionally substituted —(O)$C_{1-6}$alkyl$C_{4-12}$ cycloalkyl, optionally substituted —(O)$C_{4-12}$ heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl $C_{5-12}$aryl, optionally substituted —(O)$C_{1-12}$ heteroaryl, and optionally substituted —(O)$C_{1-6}$alkyl$C_{1-12}$heteroaryl.

Any undefined valency on an atom of a structure shown in this application implicitly represents a hydrogen atom bonded to the atom.

In some embodiments, the tyramine containing hydroxycinnamic acid amide has a structure of Formula IV:

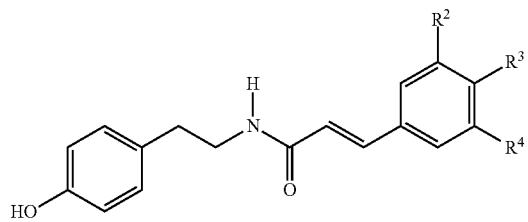

Formula IV wherein, $R^2$ is present or absent, and when present is a hydroxy or methoxy group;

$R^3$ is present or absent, and when present is a hydroxyl group or methoxy group; and $R^4$ is present or absent, and when present is a hydroxy or methoxy group.

"Isomer" refers to especially optical isomers (for example essentially pure enantiomers, essentially pure diastereomers, and mixtures thereof) as well as conformation isomers (i.e., isomers that differ only in their angles of at least one chemical bond), position isomers (particularly tautomers), and geometric isomers (e.g., cis-trans isomers).

In some embodiments, the disclosure encloses a compound of Formula (V):

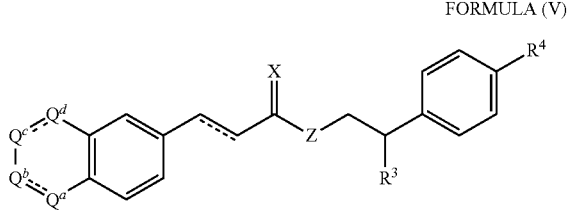

FORMULA (V)

In some embodiments, $R^3$ and $R^4$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$ alkyl, optionally substituted —(O)$C_{1-6}$alkenyl, optionally substituted —(O)C$_{1-6}$alkynl, optionally substituted, —(O)C$_{4-12}$cycloalkyl, optionally substituted —(O)C$_{1-6}$alkylC$_{4-12}$cycloalkyl, optionally substituted —(O)C$_{4-12}$heterocyclyl, optionally substituted —(O)C$_{1-6}$alkylC$_{2-12}$heterocyclyl, optionally substituted —(O)C$_{5-12}$aryl, optionally substituted —(O)C$_{1-6}$alkylC$_{5-12}$aryl, optionally substituted —(O)C$_{1-12}$heteroaryl, and optionally substituted —(O)C$_{1-6}$alkylC$_{1-12}$heteroaryl.

In some embodiments, the each independently selected dashed bond is present or absent.

In some embodiments, Z is CHR$^a$, NR$^a$, or O.

In some embodiments, R$^a$ is selected from hydrogen, deuterium, hydroxyl, halogen, cyano, nitro, optionally substituted amino, optionally substituted C-amido, optionally substituted N-amido, optionally substituted ester, optionally substituted —(O)C$_{1-6}$alkyl, optionally substituted —(O)C$_{1-6}$alkenyl, optionally substituted —(O)C$_{1-6}$alkynl, optionally substituted —(O)C$_{4-12}$ cycloalkyl, optionally substituted —(O)C$_{4-12}$ heterocyclyl, optionally substituted —(O)C$_{4-12}$ cycloalkyl, optionally substituted —(O)C$_{1-6}$alkylC$_{5-12}$ aryl, optionally substituted —(O)C$_{1-6}$alkylC$_{5-12}$ heteroaryl.

In some embodiments, Q$^a$, Q$^b$, Q$^c$, Q$^d$ are each independently selected from a bond, CHR$^a$, NR$^a$, C=O, and —O—.

In some embodiments, R$^a$ is selected from hydrogen, deuterium, hydroxyl, halogen, cyano, nitro, optionally substituted amino, optionally substituted C-amido, optionally substituted N-amido, optionally substituted ester, optionally substituted —(O)C$_{1-6}$alkyl, optionally substituted —(O)C$_{1-6}$alkenyl, optionally substituted —(O)C$_{1-6}$alkynl, optionally substituted, —(O)C$_{4-12}$ cycloalkyl, optionally substituted —(O)C$_{1-6}$alkylC$_{4-12}$ cycloalkyl, optionally substituted —(O)C$_{4-12}$ heterocyclyl, optionally substituted —(O)C$_{1-6}$alkylC$_{4-12}$heterocyclyl, optionally substituted —(O)C$_{4-12}$aryl, optionally substituted —(O)C$_{1-6}$alkyl C$_{5-12}$aryl, optionally substituted —(O)C$_{1-12}$ heteroaryl, and optionally substituted —(O)C$_{1-6}$alkylC$_{1-12}$heteroaryl.

In some embodiments, Q$^c$, Q$^d$ are absent. In some embodiments, Q$^d$ is absent.

In some embodiments, n is 1, 2, 3, or 4

In some embodiments, the compound of Formula I, II, III, and IV are selected from caffeoyltyramine, feruloyltyramine, coumaroyltyramine, cinnamoyltyramine, sinapoyltramine, and 5-hydroxyferuloyltyramine. In some embodiments, the compound of Formula I, II, III, and IV are selected from n-caffeoyltyramine, n-feruloyltyramine, n-coumaroyltyramine, n-cinnamoyltyramine, n-sinapoyltyramine, and 5-hydroxyferuloyltyramine. In some embodiments, the tyramine containing hydroxycinnamic acid amide is one of the following compounds:

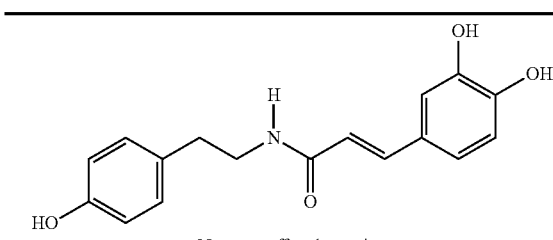

N-trans-caffeoyltyramine

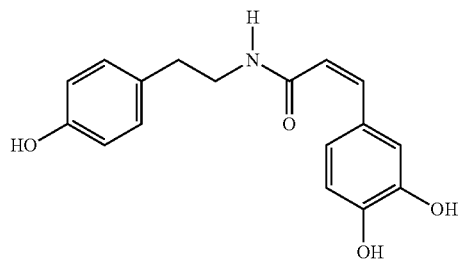 [SMILES: O=C(/C=C\c1ccc(O)c(O)c1)NCCc1ccc(O)cc1]

N-cis-caffeoyltyramine

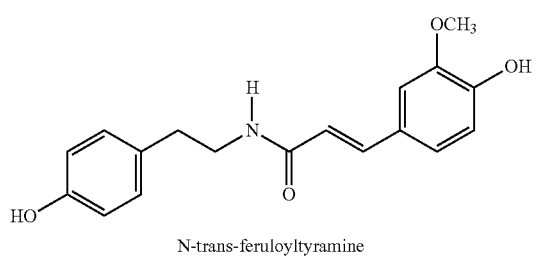

N-trans-feruloyltyramine

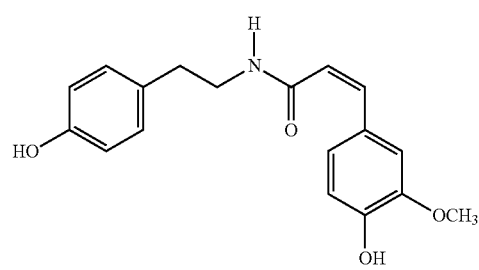 [SMILES: COc1cc(/C=C\C(=O)NCCc2ccc(O)cc2)ccc1O]

N-cis-feruloyltyramine

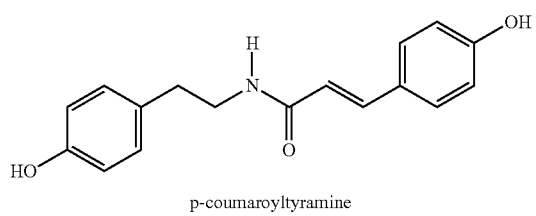

p-coumaroyltyramine

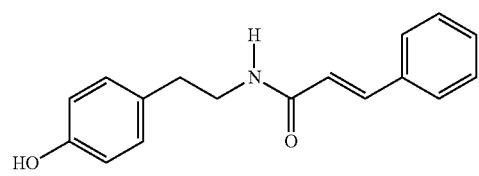 [SMILES: O=C(/C=C/c1ccccc1)NCCc1ccc(O)cc1]

cinnamoyltyramine

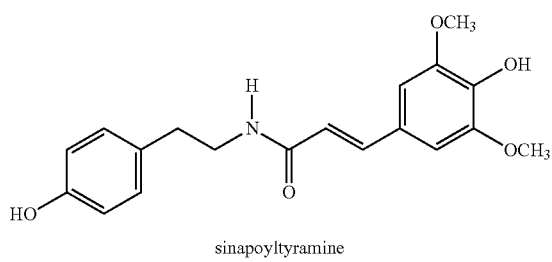

sinapoyltyramine

-continued

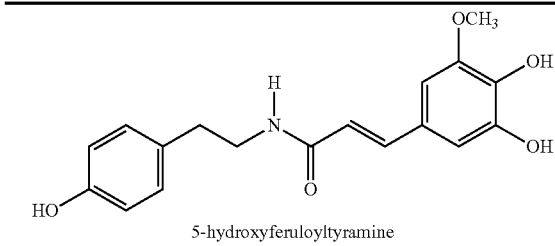
5-hydroxyferuloyltyramine

The biosynthesis of hydroxycinnamic acid amides of tyramine by higher plants is via the phenylpropanoid pathway, specifically the hydroxycinnamic acid tyramine amide biosynthesis pathway, which involves coupling of a tyramine moiety and a hydroxycinnamic acid-derived moiety. The amide coupling reaction is performed by tyramine-N-hydroxycinnamoyltransferase (formerly referred to as tyramine-N-feruloyltransferase), or THT (E.C. 2.3.1.110), which condenses the activated Coenzyme A (CoA) form of the specific hydroxycinnamic acid derivative together with tyramine.

Tyramine and hydroxycinnamic acid moieties are both produced through the shikimic acid pathway that yields aromatic amino acids and folate compounds. Tyrosine, the precursor of tyramine is produced from prephenate, an intermediate in the shikimic acid pathway in the plastid of the plant. Prephenate, derived from the central shikimic acid pathway intermediate chorismite via chorismite mutase, is converted to arogenate through a transaminase reaction via glutamate prephenate aminotransferase (E.C. 2.6.1.79), using glutamine as the amine donor, or aspartate prephenate aminotransferase (E.C. 2.6.1.78), using asparagine as the amine donor. Arogenate is then converted to tyrosine via arogenate dehydratase (E.C. 4.2.1.91) or arogenate dehydrogenase (E.C. 1.3.1.43). Finally, tyrosine is converted to tyramine via tyrosine decarboxylase (E.C. 4.1.1.25).

Hydroxycinnamic acid moieties are produced through conversion of phenylalanine, which, like tyrosine, is produced from arogenate via arogenate dehydratase. Phenylalanine is then converted to trans-cinnamate via phenylalanine ammonia lyase (E.C. 4.3.1.24), which catalyzes a deamination step. Trans-cinnamate is converted to 4-hydoxycinnamate via trans-cinnamate 4-monooxygenase (E.C. 1.14.14.91). 4-Hydroxycinnamate and Coenzyme A are then converted to 4-coumaroyl-CoA via 4-coumarate ligase (E.C. 6.2.1.12). Activated CoA forms of the other hydroxycinnamate family members, including caffeic acid and ferulic acid, are derived from 4-coumaroyl-CoA.

Hydroxycinnamic acid amides of tyramine are synthesized by condensation of cinnamoyl-CoA, p-coumaroyl-CoA, caffeoyl-CoA, feruloyl-CoA, and sinapoyl-CoA with tyramine via tyramine-N-hydroxycinnamoyltransferase (E.C. 2.3.1.110), also known as tyramine-N-feruloyltransferase, to yield cinnamoyltyramine, p-coumaroyltyramine, N-caffeoyltyramine, N-feruloyltyramine, and sinapoyltyramine, respectively. A schematic of the biochemical pathways is provided in FIG. 1.

Figure 2:
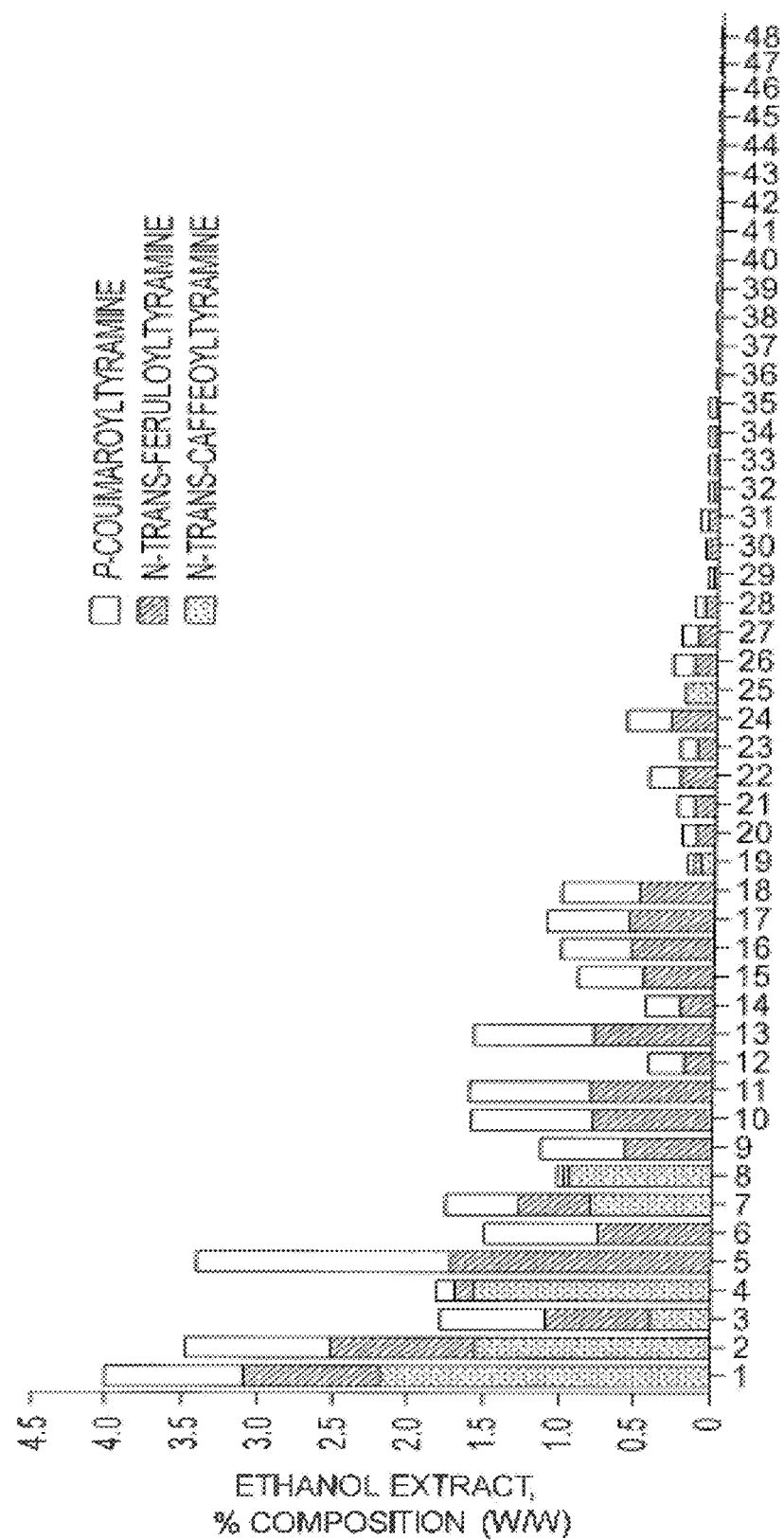
FIG. 2 shows the amounts of N-trans-caffeoyltyramine, N-trans-feruloyltyramine and p-coumaroyltyramine present in ethanol extracts (% of extract, w/w) from a variety of sources including *Tribulus terrestris* seed (1), *Cannabis* (hemp) seed hull (2), *Annona* spp. (atemoya) seed (3), *Annona muricata* (guanabana) seed (4), *A. cherimola* (Cherimoya) leaf (5), *Zea mays* stalk (6), *Tribulus terrestris* (Goat Head) seed (7), *A. cherimola* hardwood (bark and core) (8), *Solanum lycopersicum* ground pomace (9), *S. tuberosum* (yellow potato) peel (10), *Piper nigrum* (black peppercorn) fruit (11), *S. tuberosum* (purple potato) peel (12), *S. tuberosum* (red potato) peel (13), *S. lycopersicum* pomace (14), *S. lycopersicum* extruded pomace (15), *A. muricata* (guanabana) leaves (16), *Allium sativum* (garlic) bulb (17), *S. tuberosum* (purple potato) peel (18), *A. montana* (Mountain soursop) leaves (19), *Z. mays* leaves (20), *S. tuberosum* (purple potato) sprouts (21), *A. cherimola* (Cherimoya) seed (22), *Allium fistulosum* (green onion) whole plant (23), *S. tuberosum* (white potato) peel (24), *A. cherimola* (Cherimoya) greenwood (25), *Cannabis* (hemp) leaves (26), *S. tuberosum* (white potato) peel (27), *S. lycopersicum* seed (28), *S. lycopersicum* (Beefsteak) whole fruit (29), *A. muricata* (guanabana) skin of unripe fruit (30), *A. muricata* (guanabana) ripe fresh fruit (31), *A. squamosa* (sweetsop) whole fruit (32), *Capsicum annuum* (serrano pepper) fruit (33), *S. tuberosum* (Russet potato) peel (34), *Lycium barbarum* (goji/wolf berry) fruit (35), *S. tuberosum* (purple potato) core (36), *Chenopodium quinoa* (quinoa) seed (37), *Ipomoea batatas* (sweet potato) whole potato (38), *Ipomoea batatas* (sweet potato) peel (39), *Armoracia rusticana* (horseradish) root (40), *S. tuberosum* (Colorado potato) peel (41), *Fagopyrum esculentum* (buckwheat) hulls (42), *Capsicum frutescens* (piri pepper) fruit (43), *S. tuberosum* (purple potato) core (44), *C. annuum* (Thai chili) stems and leaves (45), *A. muricata* (guanabana) unripe fruit flesh (46), *S. tuberosum* (yellow potato) core (47), and *Eragrostis tef* (teff) seed (48).

While in principle any plant may be used in accordance with the present disclosure, tyramine containing hydroxycinnamic acid amides have been shown to be synthesized in plants from genera including Solanum sp. (e.g., tomato, potato, nettle, chili pepper, and eggplant), Capsicum (e.g., piri piri pepper and searrano pepper), Allium sp. (e.g., garlic, onion, and leek), Tribulus sp. (e.g., puncture vine) and Annona sp. (e.g., cherimoya, custard apple and sweetsop). Of the plant species tested, most were found to produce the compounds of interest in titers of less than 1% in an ethanol extract by weight (FIG. 2). In particular, Annona muricata (guanabana) was found to produce the highest levels of N-trans-caffeoyltyramine and p-coumaroyltyramine, but only low levels of N-trans-feruloyltyramine. By comparison, Annona atemoya produced the second highest titer of N-trans-caffeoyltyramine and high titers of both p-coumaroyltyramine and N-trans-feruloyltyramine. Further, red potato peels (Solanum tuberosum) contained trace quantities of N-trans-caffeoyltyramine, high levels of N-trans-feruloyltyramine and the highest titer of p-coumaroyltyramine. Green onion displayed the second highest quantities of p-coumaroyltyramine (second to potato peels), modest levels of N-trans-feruloyltyramine, and no detectable amount of N-trans-caffeoyltyramine.

In accordance with one aspect of the present disclosure, a plant is subjected to at least one biotic or abiotic stress or stimulus in order to increase the content of phenolic compounds, especially tyramine containing hydroxycinnamic acid amides and/or substrates for the production thereof. The term "plant" includes whole plants; plant parts such as shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary); plant tissue (for example, vascular tissue, ground tissue, and the like); and cells (for example, guard cells, egg cells, and the like), and progeny and cultures or cell lines of the same.

The plant can be subjected to at least one biotic or abiotic stress or stimulus pre- and/or post-harvest and subsequently be used for the preparation of plant-derived extracts including juices, infusions, and fermentation residues. The products fermentation plant-derived extracts or processed fractions thereof (e.g., including purified tyramine containing hydroxycinnamic acid amides) find use in consumable compositions such as health-promoting compositions or tonics for humans and animals, as well as cosmetics.

At least one used to increase hydroxycinnamic acid biotic and/or levels of amides (e.g., abiotic treatments is tyramine containing N-caffeoyltyramine, N-feruloyltyramine, p-coumaroyltyramine, cinnamoyltyramine or sinapoyltyramine) or precursors thereof in a plant. In some embodiments, more than one biotic and/or abiotic treatment is used, e.g., 2, 3, 4, 5, 6, 7, 8, 9 or 10. In other embodiments, at least one biotic or abiotic stress is applied pre-harvest and at least one biotic or abiotic stress is applied post-harvest. For the purposes of this disclosure, the term "harvest" refers to the process or period in time in which a plant or plant part is removed from its natural environment. For example, a whole plant is harvested when it is removed from the soil in which it was planted, whereas a fruit is harvested when it is removed from the whole plant.

A "biotic" stress or stimulus is defined as a stress that occurs as a result of damage done to an organism by other living organisms, such as bacteria, viruses, fungi, parasites, beneficial and harmful insects, weeds, and cultivated or native plants. For example, among the accumulating phenylpropanoids, N-hydroxycinnamoyl-tyramines have been identified both in Phytophthora infestans-infected leaves and suspension-cultured potato cells (Keller, et al. (1996) Phytochemistry 42:389-396) The P. infestans-induced pathway in potato has also been shown to occur in response to elicitor of Nicotiana glutinosa and treatment in cultured cells Eschscholtzia californica (Villegas & Brodelius (1990)

*Physiol. Plant.* 78:414-420), as well as *Nicotiana tabacum* (Negrel & Javelle (1995) *Physiol. Plant.* 95:569-574). Similarly, tomato plants inoculated with *Pseudomonas syringae* pv. tomato have been shown to accumulate p-coumaroyltyramine and feruloyltyramine (Zacares, et al. (2007) *Mol. Plant Microbe Interact.* 20(11)1439-48).

Examples of suitable biotic stimuli of use in the method of this disclosure include, but are not limited to, *Phytophthora infestans, Pseudomonas syringae, Xanthomonas campestris* pv. *vesicatoria, Erwinia carotovora* subsp. *carotovora, Ralstonia solanacearum, Pseudomonas corrugata, Alternaria, Rhizoctonia, Sclerotinia, Colletotrichum* sp., Phythium sp., *Verticillium, Fusarium* wilt, late blight, spotted wilt virus, tomato mosaic virus, fruitworm, root-knot nematode, Potato virus Y, Tomato yellow leaf curl, Tomato mosaic, Tomato mottle, black leg, powdery mildew, powdery scab, leafroll virus, Braephratiloides cubense, and thrips. Food-grade fungi such as Aspergillus sojae may also be used to enhance production of phenolic compounds.

An "abiotic" stress or stimulus is defined as a negative impact of a non-living factor on a living organism. Examples of abiotic stresses of use in the method of this disclosure include, but are not limited to, hyperosmotic stresses such as drought or high salt, temperature stresses such as cold or heat, aberrant nutrient conditions, mechanical shock, flooding, wounding, anaerobic stress, oxidative stress, ozone, high light, heavy metals, toxic chemicals, ultrasound, ultraviolet light, elicitor chitosan treatment, modified lecithin treatment, abscisic acid treatment, false germination and combinations thereof.

By way of illustration, nitrogen depletion, temperature, and light have been shown to synergistically increase the content of phenolic compounds and gene expression in the leaves of tomato (Lovdal, et al. (2010) *Phytochemistry* 71:605-613). Further, tyrosine decarboxylase and tyramine hydroxycinnamoyl transferase levels are increased in wounded tobacco (Hagel, & Facchini (2005) *Planta* 221: 904-914) and potato tuber discs (Negrel, et al. (1993) *J. Plant Physiol.* 142(5):518-524) with concurrent in vivo production of amides of ferulic acid with tyramine or octopamine. Moreover, elicitor chitosan treatment has been shown in increase coumaroyl tyramine in potato (Schmidt, et al. (1999) *J. Biol. Chem.* 274:4273-4280).

Hyperosmotic stresses include exposure to drought, high salt or high solute conditions. Whereas drought can be achieved by reducing or eliminating the amount of water a plant receives, a high salt or hyperosmotic condition can include exposing a plant to a solution containing, e.g., at least 150 mM NaCl or at least 300 mM mannitol. A plant can be flooded or water logged by covering or submerging the plant in water.

Temperature stress includes exposure to either high or low temperature. Low temperature or freezing stress may be conditions in which the average temperature of the plant environment is 15° C. or lower, and still more severely 5° C. more severely 10° C. or lower, or lower. High temperature stress may be conditions in which an average temperature of the plant environment is 25° C. or higher, more severely 300 or higher, and still more severely 35° C. or higher.

Aberrant nutrient conditions refer to high or low nitrogen, phosphorus, iron and the like.

The term "anaerobic stress" means any reduction in oxygen levels sufficient to produce a stress as hereinbefore defined, including hypoxia and anoxia.

Oxidative stress refers to any stress, which increases the intracellular level of reactive oxygen species.

Wounding is the irreversible disturbance of the natural plant, tissue and/or cell structure by methods like cutting, slicing, abrasion, squashing, breaking, peeling, crushing, pressing, slashing, grinding, fluid injection, osmotic shock, detaching, shredding, rubbing, piercing, pinching and tearing.

Ultraviolet light has been reported to be an abiotic stress that induces an increase in phenolic compounds. UVB has been the most frequently used source of irradiation for increasing phenol antioxidant production in plants. The UVB spectral band (280-315 μm) contributes less than 2% of the short-wave photons in sunlight. Post-harvest application of UVB irradiation at light ranges from about 10 mW/cm$^2$ to about 50 mW/cm$^2$ can be carried out by known methods (Huyskens-Keil (2007) *J. Appl. Bot. Food Qual.* 81:140-144; Eichholz (2011) *Food Chem.* 126:60-64) UVC treatment (100-280 nm) at light ranges from about 1 mW/cm$^2$ to about 25 mW/cm$^2$ can also be used to induce production of phenolics in accordance with known methods (Cantos, et al. (2000) *J. Agric. Food Chem.* 48:4606-4612). Irradiation durations depend on the UV intensity and in certain embodiments will range from about 10 minutes to about 3 hours, with some durations between 30 minutes and 1 hour. The durations and intensities can be determined using routine skill in the art and will vary depending on the commercial set up for handling large quantities of plant material. In certain embodiments, irradiation is conducted at temperatures ranging from about 20-40° C.

False germination or false malting treatment similar or identical to malting describes a technique as practiced by a person skilled in the art. However, as the seeds are in dormancy, for example in secondary dormancy, the seeds subjected to false malting do not germinate. See U.S. Pat. No. 10,334,689 B2, incorporated herein by reference.

The step of applying biotic or abiotic stress to a plant induces the expression of key enzymes and/or increases pools of enzyme substrates, which in turn leads to formation and accumulation of the desired compound or class of compounds of Formula I. Indeed, as the data provided herein demonstrates, wounding of *Solanum tuberosum* tubers was found to provide a 33-fold increase in N-trans-caffeoyltyramine production.

In accordance with another aspect of this disclosure, the level of one or more tyramine containing hydroxycinnamic acid amides in a plant or extract are enhanced by contacting an extract or source plant material including one or more precursors of the tyramine containing hydroxycinnamic acid amides with an enzymatic material including one or more endogenous enzymes that convert the one or more precursors to one or more tyramine containing hydroxycinnamic acid amides. In certain embodiments, the extract or source material and enzymatic material is obtained from different sources, e.g., two or more different tissues of the same plant, tissues from two or more different plants, or a plant and a microbe. In some embodiments, a source material including one or more precursors of the tyramine containing hydroxycinnamic acid amides is contacted with a source material containing one or more endogenous enzymes that convert the one or more precursors to one or more tyramine containing hydroxycinnamic acid amides. In another embodiment, a source material including one or more precursors of the tyramine containing hydroxycinnamic acid amides is contacted with an extract containing one or more endogenous enzymes that convert the one or more precursors to one or more tyramine containing hydroxycinnamic acid amides. In a further embodiment, an extract including one or more precursors of the tyramine containing hydroxycinnamic acid amides is contacted with an extract containing one or more endogenous enzymes that convert the one or more precursors to one or more tyramine containing hydroxycinnamic acid amides.

An "extract" refers a composition containing a desired compound of interest which is separated from other substances present in the natural source material from which the composition was obtained. In some embodiments, the natural source material is a plant, microbe or animal. In certain embodiments, the extract is a bacterial or fungal extract. In other embodiments, the extract is a plant extract. Plant extracts can be obtained from any plant tissue including a whole plant; plant part such as shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary); plant tissue (for example, vascular tissue, ground tissue, and the like); or cell (for example, guard cells, egg cells, and the like), and progeny and cultures or cell lines of the same. In some embodiments, the extract is generally recognized as safe for human consumption. Accordingly, in certain embodiments the extract is from an edible source. In this respect, the extract is an edible extract.

Extracts can be prepared by freezing, grinding, macerating, pulverizing and/or fermenting the source material of interest, subjecting the source material to solvent extraction, and separating the insoluble material from soluble material. In this respect, an "extract" of the disclosure can be crude, fractionated, sub-fractionated, separated, isolated, enriched or purified, without being limited thereto. The term "crude" means compounds or molecules that have not been entirely separated from the components of the original composition in which it was present. In embodiments pertaining to fractions or sub-fractions, a molecule in crude extract may be subjected to partial separation to provide a less crude extract containing other substances. By comparison, the term "isolated" means that a compound or molecule is substantially enriched or purified with respect to the complex cellular milieu in which it naturally occurs, such as in a crude extract. When an isolated molecule is enriched or purified, the absolute level of purity is not critical and those skilled in the art can readily determine appropriate levels of purity according to the use to which the material is to be put. In some circumstances, the isolated molecule forms part of a composition (for example a more or less crude extract containing many other substances), which may for example contain other components. In other circumstances, the isolated molecule may be purified to essential homogeneity, for example as determined spectrophotometrically, by NMR or by chromatography (for example LC-MS).

Suitable solvents for preparing an extract include, e.g., n-pentane, hexane, butane, chloroform, dichloromethane, di-ethyl ether, acetonitrile, water, butanol, isopropanol, ethanol, methanol, glacial acetic acid, acetone, norflurane (HFA134a), ethyl acetate, dimethyl sulfoxide, heptafluoropropane (HFA227), and subcritical or supercritical fluids such as liquid carbon dioxide and water, or a combination thereof in any proportion. When solvents such as those listed above are used, the resultant extract typically contains non-specific lipid-soluble material. This can be removed by a variety of processes including "winterization", which involves chilling to a specified temperature, typically −20° C. followed by filtration or centrifugation to remove waxy ballast, extraction with subcritical or supercritical carbon dioxide or non-polar solvents (e.g., hexane) and by distillation.

An "extract including one or more precursors of the tyramine containing hydroxycinnamic acid amides" refers to an extract including one or more of the precursors shown in FIG. 1, i.e., tyrosine, phenylalanine, tyramine, cinnamoyl-CoA, cinnamate, p-courmaric acid, p-coumaroyl-CoA, caffeic acid, caffeoyl-CoA, ferulic acid, feruloyl-CoA, sinapic acid and/or sinapoyl-CoA. Any natural source of these precursors can be used to provide an extract in accordance with this disclosure. By way of illustration, natural sources of p-coumaric acid include, but are not limited to, peanuts, navy beans, tomatoes, carrots, basil, garlic and barley. Further, natural sources of caffeic acid include, but are not limited to, coffee, turmeric, basil, thyme, oregano, sage, cabbage, apples, strawberries, cauliflower, radishes, green onion, mushrooms, kale and pears. Moreover, natural sources of ferulic acid include popcorn, tomato, garlic, navy bean, bamboo shoots, and cooked sweetcorn. In addition, hydroxycinnamic acid-rich sources include, amongst others, grains, cereals, fruits, vegetables and herbs. Cheese is also a source of one or more precursors.

An "enzymatic material including one or more endogenous enzymes that convert the one or more precursors to one or more tyramine containing hydroxycinnamic acid amides" refers to an fraction, sub-fraction, extract (as described herein), isolated enzyme, enzyme complex, bacterial cell, fungal cell, plant cell, or plant tissue culture that endogenously includes (e.g., expresses) one or more of the enzymes shown in FIG. 1, i.e., PAL, C4H, 4CL, C3H, CCoA3H, CCoAOMT, F5H, COMT, THT, TAL, PAH, and/or TYDC. While in principle any plant may be used to supply the enzymatic material of the present disclosure, hydroxycinnamic acid amides of tyramine have been shown to be synthesized in plants from genera including *Solanum* sp. (e.g., tomato, potato, nettle, chili pepper, and eggplant), *Allium* sp. (e.g., garlic, onion, and leek), *Tribulus* sp. (e.g., puncture vine) and *Annona* sp. (e.g., cherimoya, custard apple and sweetsop) Of the plant species tested, most were found to produce the compounds of interest in titers of less than 1% in an ethanol extract by weight (FIG. 2). In particular, *Annona murica* ta (*guanabana*) was found to produce the highest levels of N-trans-caffeoyltyramine and p-coumaroyltyramine, but only low levels of N-trans-feruloyltyramine. By comparison, *Annona atemoya* produced the second highest titer of N-trans-caffeoyltyramine and high titers of both p-coumaroyltyramine and N-trans-feruloyltyramine. Further, red potato peels (*Solanum tuberosum*) contained trace quantities of N-trans-caffeoyltyramine, high levels of N-trans-feruloyltyramine and the highest titer of p-coumaroyltyramine. Green onion displayed the second highest quantities of p-coumaroyltyramine (second to potato peels), modest levels of N-trans-feruloyltyramine, and no detectable amount of N-trans-caffeoyltyramine.

Moreover, tyramine is also produced by microbial-catalyzed decarboxylation of tyrosine. Various fermentative microorganisms, especially the lactic acid bacteria, express the tdcA gene, which encodes for the tyrosine decarboxylase enzyme. An example of this activity is found in the bioconversion of tyrosine to tyramine by the *Enterococcus durans* which is found in cheese products.

To produce the desired tyramine containing hydroxycinnamic acid amides of this disclosure, certain embodiments include contacting the extract or source material with the enzymatic material. In the context of this disclosure, "contacted" or "contacting" refers to the bringing together of the extract or source material and enzymatic material to facilitate the conversion of precursors to one or more tyramine containing hydroxycinnamic acid amides. In some embodiments, contact can be achieved by passing the extract over a solid surface with the enzymatic material bound thereto. In other embodiments, contact can be achieved by mixing the extract or source material with a microbe that expresses one or more endogenous enzymes that convert the one or more precursors to one or more tyramine containing hydroxycinnamic acid amides. In certain embodiments, the mixing of an extract or source material with a microbe that expresses one or more endogenous enzymes that convert the one or more precursors to one or more tyramine containing hydroxycinnamic acid amides further includes supplementing the mixture with tyrosine. In a further embodiment, contact can be achieved by mixing the extract or source material with a second extract, e.g., a plant extract, or source material that includes one or more endogenous enzymes that convert the one or more precursors to one or more tyramine containing hydroxycinnamic acid amides. Ideally, contact of the extract or source material with the enzymatic material yields an enhanced level or one or more tyramine containing hydroxycinnamic acid amides compared to the same extract or source material not contacted with the enzymatic material. In embodiments wherein it is desirable to regulate production of the tyramine containing hydroxycinnamic acid amides, enzymatic activity can be enhanced by the inclusion of cofactors, modulated by pH or temperature, and/or stopped by subjecting the enzyme to an enzyme deactivation step, e.g., heat treatment.

In some embodiments, contact of a source material or extract with a precursor of a tyramine containing hydroxycinnamic acid amide can further enhance the production of a tyramine containing hydroxycinnamic acid amide. Accordingly, in some embodiments, the methods of this disclosure further provide for the contacting a plant, source material or extract with a precursor of a tyramine containing hydroxycinnamic acid amide including, but not limited to, tyrosine, phenylalanine, tyramine, cinnamoyl-CoA, cinnamate, p-courmaric acid, p-coumaroyl-CoA, caffeic acid, caffeoyl-CoA, ferulic acid, feruloyl-CoA, sinapic acid and/or sinapoyl-CoA.

Extracts enriched for a tyramine containing hydroxycinnamic acid amide may be use as is or further processed by precipitation, treatment with activated charcoal, evaporation, filtration, chromatographic fractionation, or a combination thereof. Extracts enriched for a tyramine containing hydroxycinnamic acid amide are ideally obtained by chromatographic fractionation. Chromatographic fractionation typically includes column chromatography and may be based on molecular sizing, charge, solubility and/or polarity. Depending on the type of chromatographic method, column chromatography can be carried out with matrix materials composed of, for example, dextran, agarose, polyacrylamide or silica and can include solvents such as dimethyl sulfoxide, pyridine, water, dimethylformamide, methanol, saline, ethylene dichloride, chloroform, propanol, ethanol, isobutanol, formamide, methylene dichloride, butanol, acetonitrile, isopropanol, tetrahydrofuran, dioxane, chloroform/dichloromethane, etc.

As an alternative, or in conjunction with chromatography, crystallization may be performed to obtain high purity tyramine containing hydroxycinnamic acid amides. The solubility of the tyramine containing hydroxycinnamic acid amide is adjusted by changing temperature and/or the composition of the solution, for instance by removing ethanol, and/or adjusting the pH to facilitate precipitation, followed by filtration or centrifugation of the precipitated crystals or oils.

Typically, the product of the chromatographic step is collected in multiple fractions, which may then be tested for the presence of the desired compound using any suitable analytical technique (e.g., high or medium pressure chromatography, mass spectrometry). Fractions enriched in the desired compound may then be selected for further purification.

By way of illustration, an extract containing N-trans-caffeoyltyramine is obtained by grinding or pulverizing the plant material, subjecting the plant material to 80% ethanol at room temperature, filtering and concentrating the 80% ethanol extract, resuspending the concentrated extract in water, partitioning the aqueous solution with hexane, adding chloroform to the aqueous layer, and subjecting the chloroform layer to liquid chromatography with silica gel. See, e.g., Ko, et al. (2015) *Internatl. J. Mol. Med.* 36(4):1042-8.

An extract containing a tyramine containing hydroxycinnamic acid amide can be standardized using conventional techniques such as high-performance liquid chromatography (HPLC) or high-performance thin-layer chromatography (HPTLC) The term "standardized extract" refers to an extract which is standardized by identifying characteristic ingredient(s) or bioactive marker(s) present in the extract. Characterization can be, for example, by analysis of the spectral data such as mass spectrum (MS), infrared (IR) and nuclear magnetic resonance (NMR) spectroscopic data.

A substantially pure tyramine containing hydroxycinnamic acid amide, extract containing a tyramine containing hydroxycinnamic acid amide or plant material with enhanced levels of a tyramine containing hydroxycinnamic acid amide can be incorporated into a consumable product for consumption by or administration to a subject. Suitable consumable products include, but are not limited to, a dietary supplement, food ingredient or additive, food product (e.g., a functional food), a medical food, nutraceutical or pharmaceutical composition.

Using the compositions and methods described herein, novel prepared foods and beverages enriched in tyramine containing hydroxycinnamic acid amides can be prepared, which promote good metabolic health. Accordingly, this disclosure also provides a consumable product prepared with the tyramine containing hydroxycinnamic acid amide-enriched extract or plant material. Examples of consumable products include, but are not limited to, a dietary supplement, food ingredient or additive, food product (e.g., a functional food), a medical food, nutraceutical or pharmaceutical composition.

A food ingredient or additive is an edible substance intended to result, directly or indirectly, in its becoming a component or otherwise affecting the characteristic of any food (including any substance intended for use in producing, manufacturing, packing, processing, preparing, treating, packaging, transporting, or holding food). A food product, in particular a functional food, is a food fortified or enriched during processing to include additional complementary nutrients and/or beneficial ingredients. A food product according to this disclosure can, e.g., be in the form of butter, margarine, sweet or savory spreads, biscuits, health bar, bread, cake, cereal, candy, confectionery, yogurt or a fermented milk product, juice-based and vegetable-based beverages, shakes, flavored waters, fermented beverage (e.g., Kombucha or fermented yerba mate), convenience snack such as baked or fried vegetable chips or other extruded snack products, or any other suitable food.

A dietary supplement is a product taken by mouth that contains a compound or extract of the disclosure and is intended to supplement the diet. A nutraceutical is a product derived from a food source that provides extra health benefits, in addition to the basic nutritional value found in the food. A pharmaceutical composition is defined as any component of a drug product intended to furnish pharmacological activity or other direct effect in the diagnosis, cure, mitigation, treatment, or prevention of disease, or to affect the structure or any function of the body of humans or other animals. Dietary supplements, nutraceuticals and pharmaceutical compositions can be found in many forms such as tablets, coated tablets, pills, capsules, pellets, granules, softgels, gelcaps, liquids, powders, emulsions, suspensions, elixirs, syrup, and any other form suitable for use.

In some embodiments, the enriched extract comprising a hydroxycinnamic acid amide of tyramine is combined with a carrier. The phrase "carrier" as used herein means a material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier should be compatible with the other ingredients of the formulation and not injurious to the subject. Some examples of materials that can serve as carriers include: (1) sugars, such as lactose, glucose and sucrose; (2) starches, such as corn starch and potato starch; (3) cellulose, and its derivatives, such as sodium carboxymethyl cellulose, ethyl cellulose, cellulose acetate, and hydroxyl propyl methyl cellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) surfactants, like lecithin; and (22) other non-toxic compatible substances employed in conventional formulations.

For preparing solid compositions such as tablets or capsules, the enriched extract is mixed with a carrier (e.g., conventional tableting ingredients such as corn starch, lactose, sucrose, sorbitol, talc, stearic acid, magnesium stearate, dicalcium phosphate or gums) and other diluents (e.g., water) to form a solid composition. This solid composition is then subdivided into unit dosage forms containing an effective amount of the compound of the present disclosure. The tablets or pills containing the compound or extract can be coated or otherwise compounded to provide a dosage form affording the advantage of prolonged action.

The liquid forms in which the compound or extract of the disclosure administration is incorporated for oral or parenteral include aqueous solution, suitably flavored syrups, aqueous or oil suspensions, and flavored emulsions with edible oils as well as elixirs and similar vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin. Liquid preparations for oral administration may take the form of, for example, solutions, syrups or suspensions, or they may be presented as a dry product for reconstitution with water or other suitable vehicles before use. Such liquid preparations may be prepared by conventional means with acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

Methods of preparing single dose formulations or compositions of this disclosure include the step of bringing into association an enriched extract of the present disclosure with the carrier and, optionally, one or more accessory and/or active ingredients. In general, the formulations are prepared by uniformly and intimately bringing into association an enriched extract of the present disclosure with liquid carriers, or finely divided solid carriers, or both, and then, if necessary, shaping the product. As such, the disclosed formulation may consist of, or consist essentially of an enriched extract described herein in combination with a suitable carrier.

When an enriched extract of the present disclosure is administered in the form of a pharmaceutical, nutraceutical, or dietary supplement to humans and animals, they can be given as a composition containing, for example, 0.1 to 99% of active ingredient in combination with an acceptable carrier. In some embodiments, the composition includes about 10% to about 30% of active ingredient in combination with an acceptable carrier.

A consumable product may be consumed by a subject to provide less than 100 mg of a compound disclosed herein per day. In certain embodiments, the consumable provides between 5 and 60 mg/day of a hydroxycinnamic acid amide of tyramine. The effective amount can be established by methods known in the art studies and be dependent upon bioavailability, toxicity, etc.

While it is contemplated that a consumable product contains more than one hydroxycinnamic acid amides, it is also contemplated that a consumable product includes only an individual hydroxycinnamic acid amides. It is also contemplated that one or more extracts could be combined in any relative amounts to produce custom combinations of ingredients containing two or more tyramine containing hydroxycinnamic acid amides in desired ratios to enhance product efficacy, improve organoleptic properties or some other measure of quality important to the ultimate use of the product.

The method of this disclosure advantageously provides for lower-cost production given the ability to produce a higher titer of hydroxycinnamic acid amides of tyramine than is naturally present in certain higher plant species, thereby reducing downstream processing and purification costs. In addition, using the method of this disclosure, it will be possible to produce tailored, more effective compositions than may be possible given the compositions found in certain higher plant species. In effect, a composition can be produced with customized combinations of compounds of Formula I. Additionally, plants can be treated during processing to encourage greater activity of, e.g., THT, as well as to encourage production of greater pools of substrates.

EXAMPLES

The following non-limiting examples are provided to further illustrate the present disclosure.

Example 1: Sources of Tyramine Containing Hydroxycinnamic Acid Amides

Ethanolic extracts were prepared from various plant species and plant tissues thereof. Individual compounds were identified in the extracts by extracting dry plant powder material with 95% aqueous ethanol. The ethanol extract was concentrated and adsorbed onto CELITE® (diatomaceous earth) and dry loaded onto a C18 solid phase extraction column. The extract was desalted by washing with two column volumes of water which were collected and discarded. Compounds were eluted with two column volumes of methanol and the extract was concentrated to dryness. The extract was resuspended in 1:1 acetonitrile:water prior to analysis. Synthetic standards of known concentrations were used to generate calibration curves prior to analysis. The results of this analysis are presented in Table 1.

TABLE 1

| Genus species | Plant Tissue(s) |
|---|---|
| N-Trans-caffeoyltyramine | |
| Tribulus terrestris | seed, fruit |
| Annona montana | leaf |
| Annona muricata | peel, pulp, seed |
| Annona cherimola | pulp, seed |
| Annona atemoya | seed |
| Solanum tuberosum | peel, tuber |
| Cannabis sativa | seed hull, leaf |
| Lycium barbarum | stem |
| N-Trans-feruloyltyramine | |
| Allium sativum | bulb |
| Solanum lycopersicum | fruit |
| Capsicum annuum | fruit |
| Capsicum frutescens | fruit |
| Solanum tuberosum | peel |
| Annona spp. | seed, leaf, fruit |
| Cannabis sativa | seed hull, leaf |
| Lycium barbarum | stem, fruit |
| Ipomoea batatas | tuber |
| Zea Mays | leaf, aerial plant |
| Piper nigrum | fruit |
| Dysphania ambrosioides | leaf |
| Hibiscus sabdariffa | flower |
| Piper auritum | leaf |
| Coumaroyltyramine | |
| Solanum lycopersicum | fruit |
| Allium fistulosum | whole plant |
| Annona spp. | seed, leaf, fruit |
| Allium sativum | bulb |
| Annona atemoya | seed |
| Annona montana | leaf |
| Annona cherimola | seed, leaf, fruit |
| Annona muricata | seed, leaf |
| Cannabis sativa | seed hull, leaf |
| Solanum tuberosum | peel, tuber |
| Tribulus terrestris | seed, fruit |
| Zea mays | leaf, aerial plant |
| Dysphania ambrosioides | leaf |
| Piper auritum | leaf |

The amounts of N-trans-caffeoyltyramine, N-trans-feruloyltyramine and p-coumaroyltyramine present in certain ethanol extracts (% of extract, w/w) was determined. Quantification of the compounds was performed by normalizing the results by the weight of the ethanol extracts. The results of these analyses are presented in FIG. 2.

Figure 3:
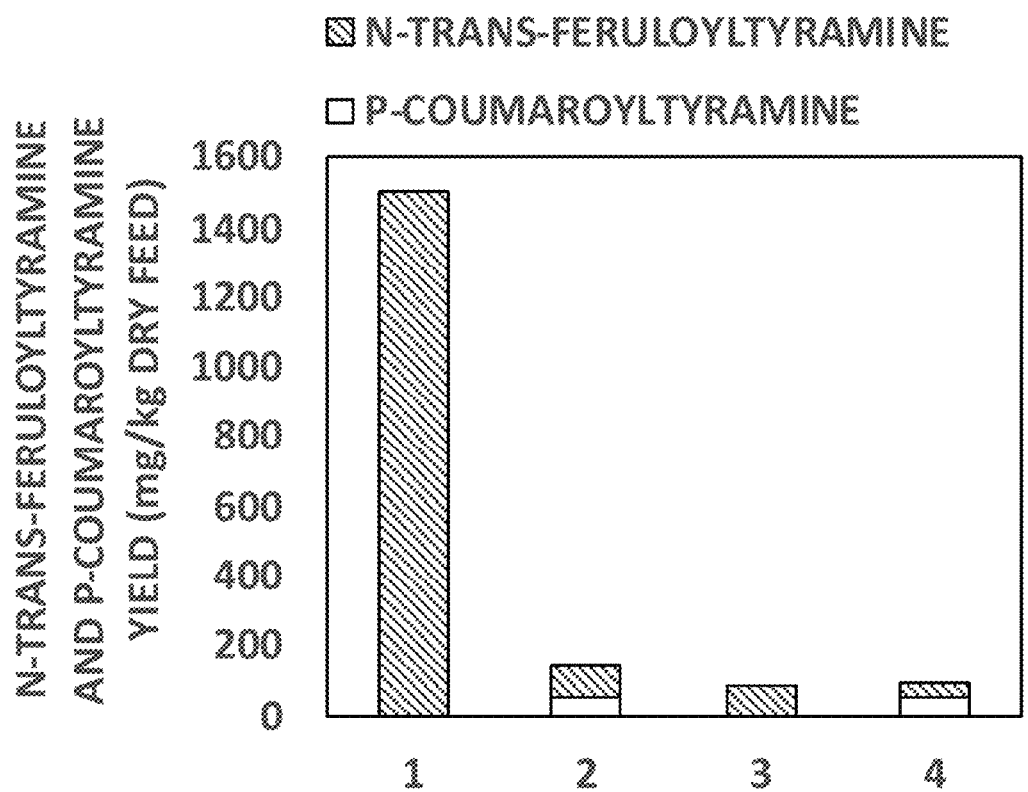
FIG. 3 shows the amounts of N-trans-feruloyltyramine and p-coumaroyltyramine present in ethanol extracts (mg compound/kg dry plant material) from additional sources including *Piper nigrum* (peppercorn) fruit (1), *Dysphania ambrosioides* (epazote) leaf (2), *Hibiscus sabdariffa* (hibiscus) roselle (3), and *Piper auritum* (hoja santa) leaf.

Subsequent analysis of additional plant tissues identified additional plant sources of N-trans-feruloytyramine and p-coumaroyltyramine (included in Table 1). This secondary analysis was performed similarly to the first, but employed a different, more sensitive analytical instrument that allowed for direct analysis of the C18 methanol eluent, without the concentration step. Those results are presented in FIG. 3. The mass extracted of each compound (in mg) is normalized by the mass of dry plant material used for extraction (in kg).

Example 2: Extracts with Enhanced Levels of Tyramine Containing Hydroxycinnamic Acid Amides Initial analytical characterization of higher plant sources of tyramine containing hydroxycinnamic acid amides indicate widely variable levels of these compounds (FIG. 2). It is known that metabolic branch points that catalyze biochemical reactions that commit substrates to specific downstream metabolic pathways often are rate-determined steps in the overall biochemical synthesis of a product of interest. It is posited that the THT step is the rate-determining step in the biosynthesis of tyramine containing hydroxycinnamic acid amides. Furthermore, it is believed that the rate of this reaction is first substrate-limited and second enzyme-limited.

Therefore, to generate extracts with higher levels of tyramine containing hydroxycinnamic acid amides, a plant source enriched in the substrates of interest, specifically the hydroxycinnamic derivative or derivatives or interest, and/or tyramine-rich source, is contacted with a plant tissue source containing the THT enzyme. Plant tissue sources of the THT enzyme include Annona sp., A. montana (mountain soursop), A. muricata and A. cherimola, Tribulus terrestris, Allium sp., A. sativa (garlic) and A. fistulosum (green onion), Solanum lycopersicum (tomato), Capsicum sp., C. annuum (Serrano pepper), and C. frutescens (Piri Piri pepper).

The THT-containing plant source and hydroxycinnamic acid-derived substrate-containing plant sources are incubated under conditions similar to the temperature and pH conditions required for optimal activity of the THT enzyme, i.e., 30° C. and a pH of 8.5. More generally, the incubation is performed using a temperature of 25-37° C. and a pH in the range of 6.5-9.5. By way of illustration, a finished food or beverage product enriched in N-trans-caffeoyltyramine is generated by incubating the THT-containing plant tissue with a caffeoyl CoA source such as Tribulus terrestris, Annona montana, Annona muricata or Annona cherimola at 30° C. and a pH of 8.5 for 1 hour. Similarly, a finished food or beverage product enriched in N-trans-feruloyltyramine, N-trans-coumaroyltyramine, or N-trans-cinnamoyltyramine THT-containing plant tissue with ferulic acid-rich, acid-rich or cinnamic acid rich sources, respectively.

Fermented beverage or food products can also be produced using microorganisms, including lactic acid bacteria, that produce tyramine, along with sources of one or more hydroxycinnamic acids, tyrosine and the THT enzyme.

Example 3: Wounding Induces Production of N-Trans-Feruloyltyramine

Figure 4:
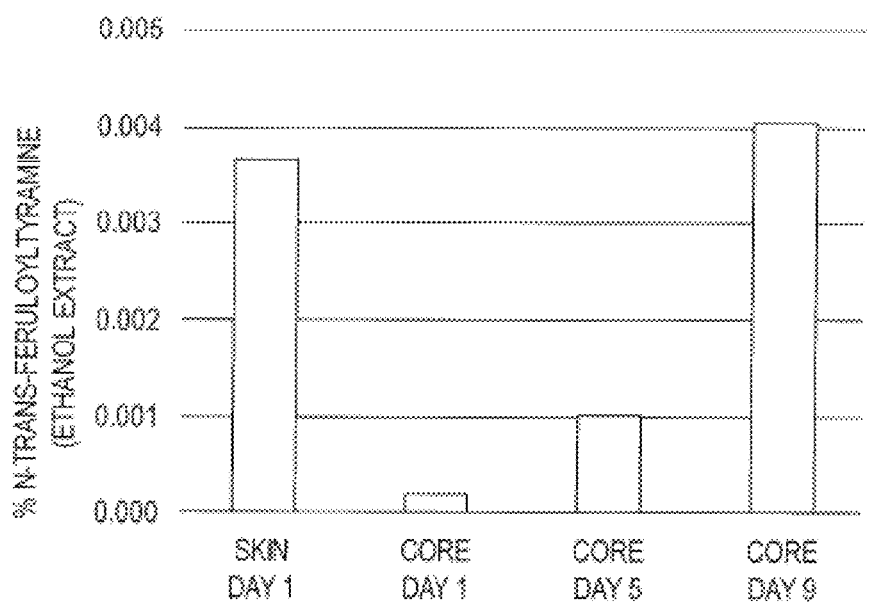
FIG. 4 shows the effect of wounding stress on the production of N-trans-feruloyltyramine in the core of a *Solanum tuberosum* tuber 1, 5 and 9 days after wounding the peeled tuber.

Initial analytical characterization of higher plant sources of a tyramine containing hydroxycinnamic acid amides indicate variable levels. It is known that metabolic branch points that catalyze biochemical reactions that commit substrates to specific downstream metabolic pathways often are rate-determined steps in the overall biochemical synthesis of a product of interest. It was posited that the THT step is rate-determining in the biosynthesis of a tyramine containing hydroxycinnamic acid amides. Furthermore, it was believed that that the rate of this reaction is first substrate-limited and second enzyme-limited. Thus, it was determined whether elevated levels tyramine containing hydroxycinnamic acid amides could be generated in situ by subjecting a plant to an abiotic stress, e.g., wounding. In particular, yellow tubers of Solanum tuberosum were wounded by wounding and production of N-trans-feruloyltyramine in the tuber was assessed 1, 5 and 9 days after wounding. The results of this analysis indicate that physical wounding of the plant tissues results in a 33-fold increase in N-trans-feruloyltyramine production (FIG. 4). Similar to yellow potato tubers, wounding of white russet, gold and purple potato peels resulted in a 178-fold, 13-fold, and 9-fold increase in N-trans-feruloyltyramine production over a 14-day period post-treatment. Further analysis indicated that oxygen was required, i.e., the potatoes could not be submerged, that citric acid/NaCl had no detrimental effect on the wounding response, and that supplying additional substrate (tyramine) enhanced the wounding response.

Figure 5A:
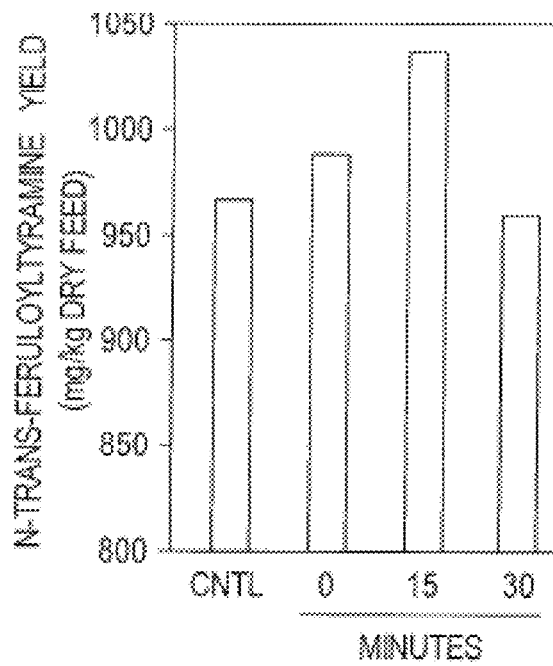
FIGS. 5A and 5B show the effect of radiation stress on the production of N-trans-feruloyltyramine in peppercorns after a 15- or 30-minute UV-C exposure (FIG. 5A) or N-trans-feruloyltyramine, N-trans-caffeoyltyramine, and p-coumaroyltyramine in graviola leaves and green onions after a 15-minute UV-C exposure (FIG. 5B) as compared to control, unexposed plant tissue (CNTL).

Example 4: UV-C Radiation Induces Production of N-Trans-Caffeoyltyramine, N-Trans-Feruloyltyramine, and p-Coumaroyltyramine The effect of radiation on levels of tyramine containing hydroxycinnamic acid amides was determined. In particular, peppercorns were exposed to UV-C radiation for 15 or 30 minutes, incubated at room temperature for six hours and subsequently assayed for N-trans-feruloyltyramine production. The results of this analysis showed a slight increase in N-trans-feruloyltyramine production yields after the 15-minute exposure to UV-C radiation (FIG. 5A).

Figure 5B:
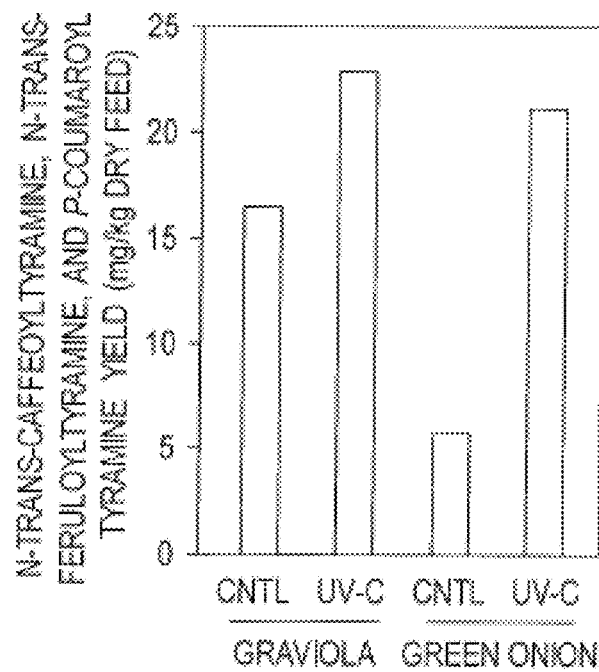

Similar analysis was carried out using graviola leaves or green onions. In this analysis, fresh plant material was subjected to direct UV-C radiation for 15 minutes and subsequently incubated in the dark (about 5 hours for graviola and overnight for green onions). The results of this analysis indicated that UV-C exposure induced a 50-300% increase in N-trans-caffeoyltyramine, N-trans-feruloyltyramine, and p-coumaroyltyramine production (FIG. 5B).

Figure 6:
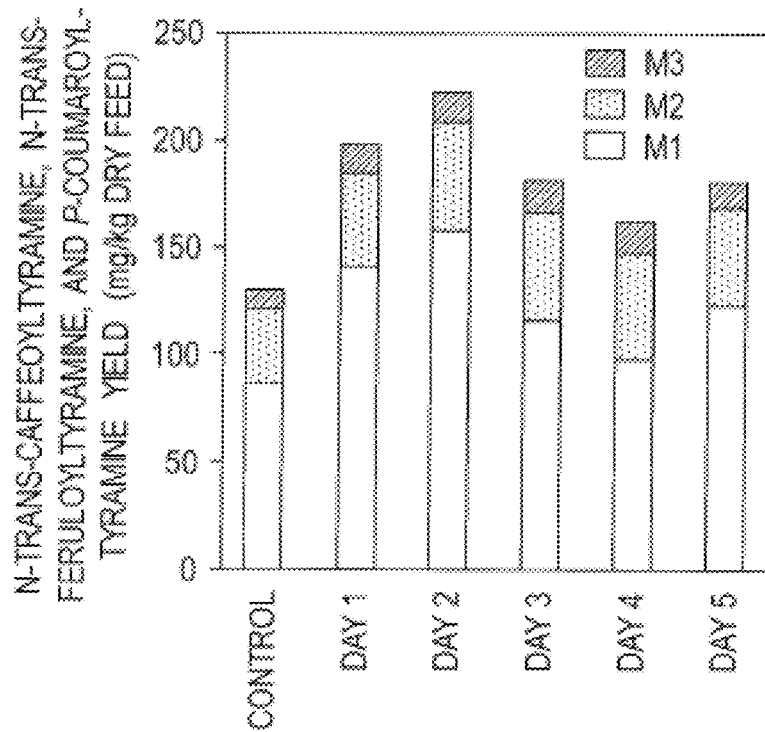
FIG. 6 shows the effect of false germination of hemp seeds on tyramine containing hydroxycinnamic acid amide production. Toasted hemp seeds were soaked in distilled water for 5 days and sampled daily for N-trans-caffeoyltyramine (M1), N-trans-feruloyltyramine (M2), or p-coumaroyltyramine (M3).

Example 5: False Germination Induces Production of N-Trans-Caffeoyltyramine, N-Trans-Feruloyltyramine, and p-Coumaroyltyramine The effect of false germination on levels of tyramine containing hydroxycinnamic acid amides in hemp seeds was determined. Toasted hemp seeds were soaked in distilled water overnight. The water was drained, and the seeds were rinsed in fresh distilled water 2 times per day for 5 days. The seeds were maintained in a moist, dark environment over the time course of the experiment and a sample of seeds was collected every day. For each sample collected, the seeds were dried, cracked and treated with hexane to remove fats. The material was subsequently milled and analyzed for N-trans-feruloyltyramine, p-coumaroyltyramine, or N-trans-caffeoyltyramine production. This analysis indicated that peak induction of N-trans-caffeoyltyramine, N-trans-feruloyltyramine, and p-coumaroyltyramine was at day 2 (1.7-fold increase; FIG. 6), though enrichment in these compounds was observed even on Day 1, immediately following the overnight soak.

Figure 7:
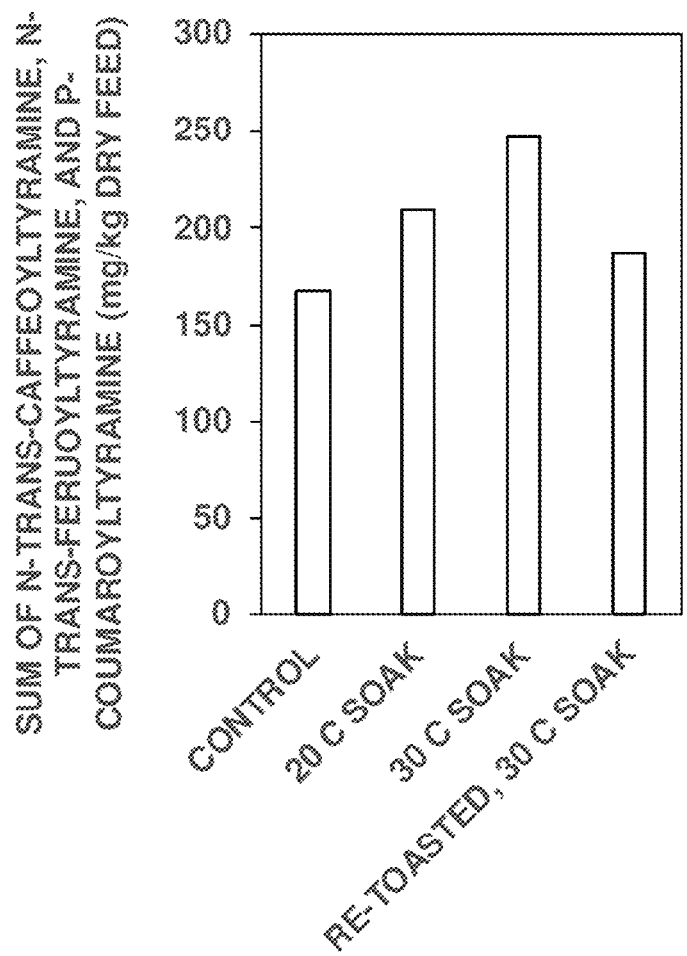
FIG. 7 shows the effect of soaking temperature and toasting conditions on the combined enrichment of N-trans-caffeoyltyramine, N-trans-feruloyltyramine, and p-coumaroyltyramine via false germination.

Additional studies show that the preliminary dry toasting temperature and the distilled water soaking temperature impact the degree of enrichment achieved (FIG. 7). Increasing the soaking temperature from 20 degrees Celsius to 30 degrees Celsius increases the combined enrichment of N-trans-feruloyltyramine, N-trans-caffeoyltyramine, and p-coumaroyltyramine from 25% to 47% greater than the control. Meanwhile, re-toasting the seeds for 10 minutes at 100 degrees Celsius prior to soaking overnight in distilled water (maintained at 30 degrees Celsius) reduces the degree of enrichment achieved to 12%, presumably because such toasting conditions inactivate enzymes that play critical roles in the false germination process.

Example 6: Combined Stresses Induce Production of N-Trans-Feruloyltyramine

Figure 8:
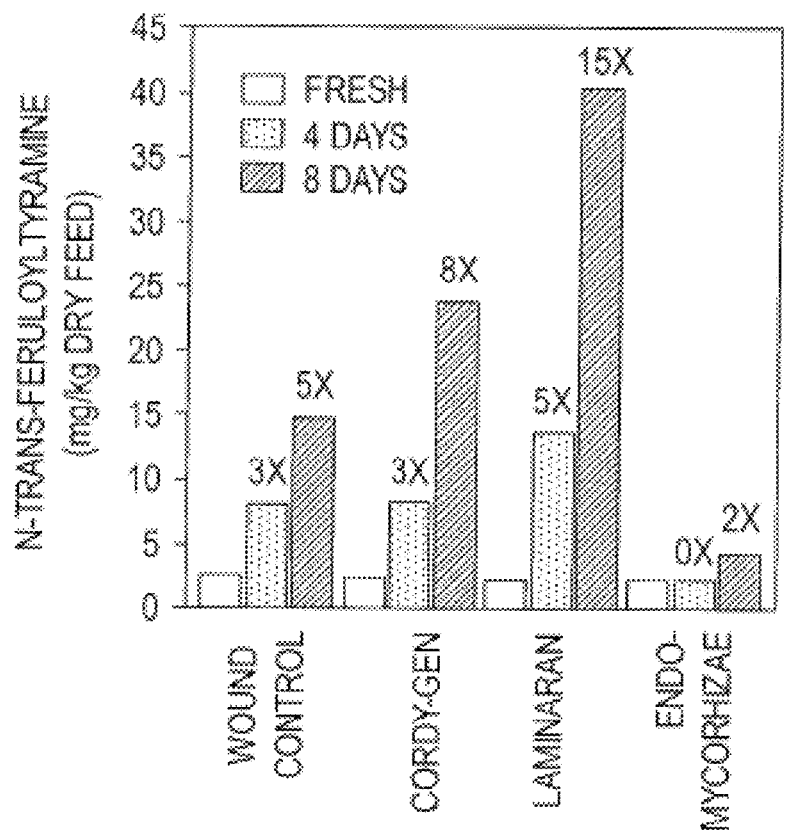
FIG. 8 shows the effect of combining different stresses on the production of N-trans-feruloyltyramine. Red potatoes were sliced (i.e., wounded) and dipped into aqueous solutions of 10 mg/ml live endomycorrhizal fungi, 10 mg/ml inactivated cordy-gen fungi, or 1 mg/ml laminaran (polysaccharide from brown algae).

Having demonstrated that wounding could increase N-trans-feruloyltyramine production, it was determined whether combining wounding with THT enzyme elicitors could further enhance N-trans-feruloyltyramine production. For this analysis, red potatoes were sliced to a standard thickness. Subsequently, the potato slices were dipped into solutions of 10 mg/ml live endomycorrhizal fungi, 10 mg/ml inactivated cordy-gen fungi (from Mycopia), 1 mg/ml laminaran (polysaccharide from brown algae) or water (control) The potato slices were loosely covered to allow for air flow and incubated for 4 or 8 days at room temperature. The results of this analysis indicated that whereas wounding in combination with laminaran exposure substantially enhanced the production of N-trans-feruloyltyramine, wounding in combination with cordy-gen provided some enhancement and live endomycorrhizae prohibited N-trans-feruloyltyramine production in response to wounding (FIG. 8).

Figure 9:
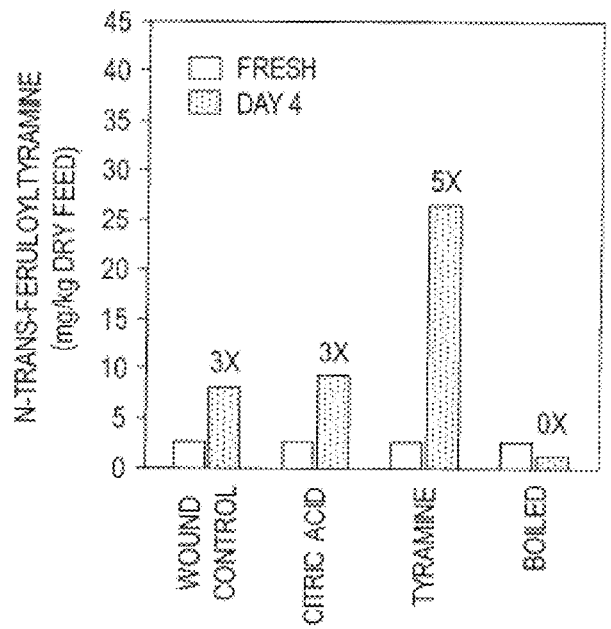
FIG. 9 shows the effect of combining a stress with a precursor on the production of feruloyltyramine. Red potatoes were sliced (i.e., and boiled in water for 6 minutes or dipped into abiotic N-trans-wounded) aqueous solutions of 400 µM tyramine or citric acid (pH ~4).

Example 7: Wounding and Precursor Exposure Induce Production of N-Trans-Feruloyltyramine Having demonstrated that wounding could increase N-trans-feruloyltyramine production, it was determined whether combining wounding with exposure to a precursor of N-trans-feruloyltyramine could further enhance N-trans-feruloyltyramine production. For this analysis, red potatoes were sliced to a standard thickness (¼ inch; two potatoes/time point). Subsequently, the potato slices were either boiled in water for 6 minutes, or dipped into aqueous solutions of 400 µM tyramine (as precursor) or citric acid (pH ~4; as a preservative), or water (control). The potato slices were loosely covered to allow for air flow and incubated for 4 days at room temperature. The results of this analysis indicated that the combination of wounding and tyramine exposure could enhance N-trans-feruloyltyramine production by day 4, whereas citric acid had little effect (FIG. 9). Notably, while the tyramine dip further increased browning of the wounded potato slices, citric acid inhibited the browning pathway without impacting the production of N-trans-feruloyltyramine.

Example 8: Assessing Stress-Induced Increases in Enzyme Activity

Biotic and/or abiotic stresses can be used to artificially induce greater abundance and activity of enzymes involved in tyramine containing hydroxycinnamic acid amide artificially induced increased supplies of substrates, or both. Enzyme activity assessments in response to biotic and/or abiotic stresses can be carried out as follows.

PAL activity is assayed in a mixture (250 µL) containing 100 mM Tris-HCl buffer pH 8.0 and enzyme extract. The reaction is initiated by the addition of 150 µL of 200 mg mL$^{-1}$ L-phenylalanine (final concentration 6 mg mL$^{-1}$) and the production of cinnamic acid is measured over 10 minutes at $\Delta A_{290}$.

C4H activity is assayed in a mixture (250 µL) containing 100 mM phosphate buffer (pH 7.5), 1 mM DTT, 1 mM NADPH, and 100 µL enzyme extract. The reaction is initiated by the addition of 10 mM trans-cinnamic acid (final concentration 1 mM) and the changes in absorbance at 290 nm are recorded during 10 minutes.

4CL activity is assayed at room temperature using a spectrophotometric assay (Knobloch & Hahlbrock (1977) *Hoffm. Arch. Biochem. Biophys.* 184:237-248) to measure formation of CoA esters, as previously described (Lee & Douglas (1996) *Plant Physiol.* 112:193-205).

THT activity is assayed using known methods (Hohlfeld, et al. (1995) *Plant Physiol.* 107:545-552). Determination of its activity is done by HPLC coupled with a photodiode array detection (Schmidt, et al. (1998) *Planta* 205:51-55).

Enzymatic activities are expressed as a function of the protein concentration of the extracts, which are assayed and calculated using the Bradford method (Bradford (1976) *Anal. Biochem.* 72:248-54). Enzymatic activities obtained are normalized against control samples and fold change of the normalized values are calculated.

What is claimed is:

1. A method for producing a consumable product with enhanced levels of a tyramine containing hydroxycinnamic acid amide, comprising:
    (a) subjecting a plant for producing a compound of Formula I

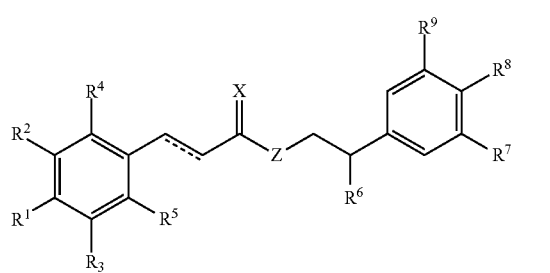

Formula I wherein
    $R^1$, $R^2$, $R^3$, $R^4$, $R^5$, $R^6$, $R^7$, $R^8$, and $R^9$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$ heterocyclyl, optionally substituted —(O)$C_{1-6}$alkyl$C_{4-12}$ heterocyclyl, optionally substituted —(O)$C_{4-12}$ aryl, optionally substituted —(O)$C_{1-6}$alkyl$C_{5-12}$ aryl, optionally substituted —(O)$C_{1-12}$ heteroaryl, and optionally substituted —(O)$C_{1-6}$alkyl$C_{1-12}$heteroaryl; the dashed bond is present or absent;
    X is $CH_2$ or O;
    Z is $CHR^a$, $NR^a$, or O; and
    $R^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl,
    the dashed bond is present or absent,
    to at least one biotic or abiotic stress;
    further subjecting the plant to air flow; and
    wherein, the subjecting is in combination with at least one enzyme, a glucan, citric acid, a fungal isolate, a tyramine solution, or a combination thereof,
    (b) incorporating the plant or extract thereof into a consumable product.

2. A method for producing a consumable product with enhanced levels of a tyramine containing hydroxycinnamic acid amide, comprising:
    (a) subjecting a plant for producing a compound of Formula II

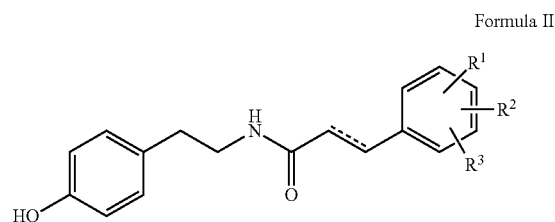

Formula II wherein
    $R^1$, $R^2$, and $R^3$ are each independently present or absent, and when present is a substituent on one or more ring atoms (e.g., position 2, 3, and/or 4) and is for each ring atom independently a hydroxy group, halo group, substituted or unsubstituted lower alkyl group, or substituted or unsubstituted lower alkoxy group,
    the dashed bond is present or absent,
    to at least one biotic or abiotic stress;
    further subjecting the plant to air flow; and
    wherein, the subjecting is in combination with at least one enzyme, a glucan, citric acid, a fungal isolate, a tyramine solution, or a combination thereof,
    (b) incorporating the plant or extract thereof into a consumable product.

3. The method of claim 1, further comprising recovering an extract from the plant.

4. The method of claim 1, further comprising contacting the plant with a precursor of a tyramine containing hydroxycinnamic acid amide.

5. The method of claim 1, wherein the biotic stress is false germination.

6. The method of claim 1, wherein the abiotic stress is selected from at least one of hyperosmotic stress, salt, temperature stresses, aberrant nutrient conditions, mechanical shock flooding, wounding, anaerobic stress, oxidative stress, ozone, high light, heavy metals, toxic chemicals, ultrasound, ultraviolet light, elicitor chitosan treatment, modified lecithin treatment, or abscisic acid treatment.

7. The method of claim 1, wherein the at least one biotic or abiotic stress comprises incubating the plant at about 25° C. to about 37° C. and a pH of 6.5 to about 9.5.

8. The method of claim 7, wherein the at least one biotic or abiotic stress comprises incubating the plant at about 30° C. and a pH of about 8.5.

9. The method of claim 6, wherein the abiotic stress is physical wounding and the compound of Formula I is n-feruloyltyramine.

10. The method of claim 9, wherein the physical wounding increases n-feruloyltyramine by at least 9-fold.

11. The method of claim 9, wherein the physical wounding increases n-feruloyltyramine by at least 13-fold.

12. The method of claim 9, wherein the physical wounding increases n-feruloyltyramine by at least 33-fold.

13. The method of claim 6, wherein the abiotic stress is ultraviolet light and the compound of Formula I is n-feruloyltyramine, n-caffeoyltyramine, and p-coumaroyltyramine.

14. The method of claim 13, wherein the plant is exposed to ultraviolet light for about 15 to about 30 minutes.

15. The method of claim 6, wherein the abiotic stress is temperature stresses and the compound of Formula I is n-feruloyltyramine, n-caffeoyltyramine, and p-coumaroyltyramine.

16. The method of claim 15, wherein the temperatures stress increases the production of n-feruloyltyramine, n-caffeoyltyramine, and p-coumaroyltyramine from about 25% to about 47%.

17. The method of claim 1, wherein the plant is selected from at least one of *Tribulus terrestris, Annona montana, Annona muricata, Annona cherimola, Annona atemoya, Solanum tuberosum, Cannabis sativa, Lycium barbarum, Allium sativum, Solanum lycopersicum, Capsicum annuum, Capsicum frutescens, Solanum tuberosum, Annona* spp., *Lycium barbarum, Ipomoea batatas, Zea Mays, Piper nigrum, Dysphania ambrosioides, Hibiscus sabdariffa, Piper auritum, Solanum lycopersicum,* or *Allium fistulosum.*

18. The method of claim 3, wherein recovering the extract from the plant comprises an ethanol extract.

19. The method of claim 1, wherein the abiotic stress is applied post-harvest.

20. The method of claim 1, wherein the abiotic stress is applied pre-harvest.

* * * * *